United States Patent
Clare et al.

(10) Patent No.: US 6,849,653 B2
(45) Date of Patent: Feb. 1, 2005

(54) SUBSTITUTED PYRAZOLYL BENZENESULFAMIDE COMPOUNDS FOR THE TREATMENT OF INFLAMMATION

(75) Inventors: Michael Clare, Skokie, IL (US); Lifeng Geng, Skokie, IL (US); Gunnar J. Hanson, Skokie, IL (US); He Huang, Northbrook, IL (US); Donna M. Iula, Palatine, IL (US); Shuyuan Liao, Northbrook, IL (US); Michael A. Stealey, Libertyville, IL (US); Richard M. Weier, Lake Bluff, IL (US); Suzanne Metz, Chesterfield, MO (US); Michael L. Vazquez, Ballwin, MO (US)

(73) Assignee: Pharmacia Corporation, Peapack, NJ (US)

( * ) Notice: Subject to any disclaimer, the term of this patent is extended or adjusted under 35 U.S.C. 154(b) by 1 day.

(21) Appl. No.: 10/247,021

(22) Filed: Sep. 19, 2002

(65) Prior Publication Data

US 2003/0125361 A1 Jul. 3, 2003

Related U.S. Application Data

(60) Provisional application No. 60/323,230, filed on Sep. 19, 2001.

(51) Int. Cl.$^7$ .................. A61K 31/416; C07D 231/54
(52) U.S. Cl. .................. 514/406; 548/359.1; 549/434; 549/435
(58) Field of Search .................. 548/359.1; 514/406; 549/434, 435

(56) References Cited

U.S. PATENT DOCUMENTS

| 3,940,418 | A | 2/1976 | Hamilton | 260/310 |
|---|---|---|---|---|
| 5,134,142 | A | 7/1992 | Matsuo et al. | 514/255 |
| 5,134,155 | A | 7/1992 | Connolly et al. | 514/403 |
| 5,260,328 | A | 11/1993 | Doria et al. | 514/406 |

FOREIGN PATENT DOCUMENTS

| EP | 0477049 | 3/1992 |
|---|---|---|
| EP | 0347773 | 4/1993 |
| WO | 95/15318 | 6/1995 |
| WO | 96/15317 | 6/1995 |
| WO | 96/09293 | 3/1996 |
| WO | 00/27822 | 5/2000 |
| WO | 00/59901 | 10/2000 |

OTHER PUBLICATIONS

R. Hamilton, *The Antiarrhythmic and Antiflammatory Activity of a Series of Tricyclic Pyrazoles* 1976, J. Herrocyclic Chem, 13, 545.

*Primary Examiner*—Golam M M Shameem
(74) *Attorney, Agent, or Firm*—Patricia K. Fitzsimmons; S. Christopher Bauer

(57) ABSTRACT

The present invention relates to substituted pyrazolyl derivatives, compositions comprising such, intermediates, methods of making substituted pyrazolyl derivatives, and methods for treating cancer, inflammation, and inflammation-associated disorders, such as arthritis.

3 Claims, No Drawings

SUBSTITUTED PYRAZOLYL BENZENESULFAMIDE COMPOUNDS FOR THE TREATMENT OF INFLAMMATION

The present application claims priority under Title 35, United States Code, §119 to U.S. Provisional application Ser. No. 60/323,230, filed Sep. 19, 2001, which is incorporated by reference in its entirety as if written herein.

FIELD OF THE INVENTION

The present invention in general is in the field of anti-inflammatory pharmaceutical agents and specifically relates to substituted pyrazolyl benzenesulfamide derivatives, compositions comprising such, and methods for treating cancer, inflammation, and inflammation-associated disorders, such as arthritis.

BACKGROUND OF THE INVENTION

The following description of the background of the invention is provided to aid in the understanding the invention, but is not admitted to be or describe prior art to the invention.

NF-κB is a ubiquitous transcription factor that plays a prominent role in the activation of the immune system and in stress responses by regulating the transcription of many early, inducible genes including proinflammatory cytokines, adhesion molecules, growth factors, enzymes, and receptors (Ghosh S., May, M. J., and Kopp. E (1998) *Annu. Rev. Immunol.* 16, 115–260; Zandi, E., and Karin, M. (1999) *Mol. Cell. Biol.* 19, 4547–4551; Karin, M. (1999) *J. Biol. Chem.* 274, 27339–27342). Specificity of gene expression is determined at a cellular level by a diverse array of external stimuli such as bacterial products including LPS, as well as cytokines, most importantly tumor necrosis factor-α (TNFα) and interleukin-β (IL1β). Through the synergistic interaction with other transcription factors, further specificity can be achieved while maintaining enormous potential to coordinately induce a large number of functionally related genes. NF-κB is composed of homo and heterodimers of the Rel protein family and is sequestered in an inactive form in the cytoplasm by members of the IκB family of inhibitory proteins (Ghosh S., May, M. J., and Kopp. E (1998) *Annu. Rev. Immunol.* 16, 115–260; Zandi, E., and Karin, M. (1999) *Mol. Cell. Biol.* 19, 4547–4551; Karin, M. (1999) *J. Biol. Chem.* 274, 27339–27342). IκBs mask the nuclear localization signal on NF-κB, preventing nuclear translocation and hence DNA binding to the promoter regions of responsive genes. Stimulation of cells with an agonist that activates NF-κB leads to a series of biochemical signals, ultimately resulting in the phosphorylation, ubiquitinylation, and degradation of IκBs, thereby releasing NF-κB for nuclear translocation (Ghosh S., May, M. J., and Kopp. E (1998) *Annu. Rev. Immunol.* 16, 115–260; Zandi, E., and Karin, M. (1999) *Mol. Cell. Biol.* 19, 4547–4551; Karin, M. (1999) *J. Biol. Chem.* 274, 27339–27342). Recently, two IκB kinases (IKK1 or IKKα and IKK2 or IKKβ), which phosphorylate IκBs and thereby initiate their degradation, have been cloned and characterized by a number of laboratories (Ghosh S., May, M. J., and Kopp. E (1998) *Annu. Rev. Immunol.* 16, 115–260; Zandi, E., and Karin, M. (1999) *Mol. Cell. Biol.* 19, 4547–4551; Karin, M. (1999) *J. Biol. Chem.* 274, 27339–27342). The catalytic subunits, IKK1 and IKK2, are similar structurally as well as enzymatically and exist as a heterodimer in a large protein complex referred to as the IKK signalsome (Regnier, C., Song, H., Gao, X., Goeddel, D., Cao, Z. and Rothe, M. (1997) *Cell* 90, 373–383; DiDonato, J. A., Hayakawa, M., Rothwarf, D. M., Zandi, E. and Karin, M. (1997) *Nature* 388, 548–554; Mercurio, F., Zhu, H., Murray, B. W., Shevchenko, A., Bennett, B. L., Li, J. W., Young, D. B., Barbosa, M., Mann, M., Manning, A. and Roa, A. (1997) *Science* 278, 860–866; Zandi, E. Rothwarf, D. M., Delhase, M., Hayadawa, M and Karin, M. (1997) *Cell* 91, 243–252; Woronicz, J. D., Gao, X., Cao, Z., Rothe, M. And Goeddel, D. V. (1997) *Science* 278, 866–869). A third protein, NEMO (IKKγ, IKKAP1), is a regulatory adapter protein necessary for IKK activation and kinase activity (Yamaoka, S., Courtois, G., Bessia, C., Whiteside, S. T., Weil, R., Agou, F., Kirk, H. E., Kay, R. J., and Ireal, A. (1998) *Cell* 93, 1231–1240; Rothwarf, D. M., Zandi, E., Natoli, G., Karin, M. (1998) *Nature* 395, 297; Mercurio, F., Murray, B. W., Shevchenko, A., Bennet, B. L., Young, D. B., Li, J. W., Pascual, G., Motiwala, A., Zhu, H., Mann, M and Manning, A. M. (1999) *Mol. Cell. Biol.* 2, 1526–1538). IKK1 and IKK2 are co-expressed in most human adult tissues as well as in different developmental stages of mouse embryos (Regnier, C., Song, H., Gao, X., Goeddel, D., Cao, Z. and Rothe, M. (1997) *Cell* 90, 373–383; DiDonato, J. A., Hayakawa, M., Rothwarf, D. M., Zandi, E. and Karin, M. (1997) *Nature* 388, 548–554; Mercurio, F., Zhu, H., Murray, B. W., Shevchenko, A., Bennett, B. L., Li, J. W., Young, D. B., Barbosa, M., Mann, M., Manning, A. and Roa, A. (1997) *Science* 278, 860–866; Zandi, E. Rothwarf, D. M., Delhase, M., Hayadawa, M and Karin, M. (1997) *Cell* 91, 243–252; Woronicz, J. D., Gao, X., Cao, Z., Rothe, M. and Goeddel, D. V. (1997) *Science* 278, 866–869; Hu, M. C. T., and Wang, Y. (1998) *Gene* 222, 31–40). This kinase complex appears to represent a critical, common denominator in the activation of NF-κB in a number of signal transduction pathways stimulated by a variety of agonists including cytokines, such as TNFα and IL1β, microbial products such as LPS and viral proteins such as TAX, as well as phorbol esters, oxidizing agents and serine/tyrosine phosphatases (Ghosh S., May, M. J., and Kopp. E (1998) *Annu. Rev. Immunol.* 16, 115–260; Zandi, E., and Karin, M. (1999) *Mol. Cell. Biol.* 19, 4547–4551; Karin, M. (1999) *J. Biol. Chem.* 274, 27339–27342).

IKK1 (also termed IKKα, Regnier, C., Song, H., Gao, X., Goeddel, D., Cao, Z. and Rothe, M. (1997) *Cell* 90, 373–383; DiDonato, J. A., Hayakawa, M., Rothwarf, D. M., Zandi, E. and Karin, M. (1997) *Nature* 388, 548–554; Mercurio, F., Zhu, H., Murray, B. W., Shevchenko, A., Bennett, B. L., Li, J. W., Young, D. B., Barbosa, M., Mann, M., Manning, A. And Roa, A. (1997) *Science* 278, 860–866) was cloned simultaneously by standard biochemical purification of the IκB kinase activity from TNFα stimulated HeLa S3 cells and by its interaction with the MAP3K, NF-κB inducing kinase (NIK), in a yeast two-hybrid screen. IKK1 was identified as the previously cloned serine-threonine kinase, CHUK (Connelly, M. and Marcu, K. (1995) *Cell. Mol. Biol. Res.* 41, 537–549). IKK1 (also termed IKKα) is an 85 kDa, 745 amino acid protein that contains an N-terminal serine/threonine kinase catalytic domain, a leucine zipper-like amphipathic helix, and a C-terminal helix-loop-helix domain. IKK2 (also termed IKKβ) was also cloned by standard biochemical purification, copurifying with IKK1 from TNFα stimulated HeLa S3 cells as well as by being identified in the public database from an EST clone with sequence homology to IKK1 (Mercurio, F., Zhu, H., Murray, B. W., Shevchenko, A., Bennett, B. L., Li, J. W., Young, D. B., Barbosa, M., Mann, M., Manning, A. and Roa, A. (1997) *Science* 278, 860–866; Zandi, E. Rothwarf, D. M., Delhase, M., Hayadawa, M and Karin, M. (1997) *Cell* 91, 243–252; Woronicz, J. D., Gao, X., Cao, Z., Rothe, M. And Goeddel, D. V. (1997) *Science* 278, 866–869). IKK2 is an 87 kDa, 756 amino acid protein with the same over all topology as IKK1 except for the addition of an 11 amino acid extension at the C-terminus. IKK1 and IKK2 are 52% identical overall with 65% identity in the kinase domain and 44% identity in the protein interaction domains in the C-terminus. Data obtained using transient mammalian expression analysis, by in vitro translation experiments and by coexpression in a baculoviral system reveals that IKK1 and IKK2 associate preferentially as a heterodimer through their leucine zipper motifs. Although homodimers have also been described in these systems, the heterodimer is thought to be the physiologic form of the kinase in mammalian cells (Zandi, E. Rothwarf, D. M., Delhase, M., Hayadawa, M and Karin, M. (1997) *Cell* 91, 243–252; Li, J., Peet, G. W., Pullen, S. S., Schembri-King, J., Warren, T. C., Marcu, K. B., Kehry, M. R., Barton, R. and Jakes, S. (1998) *J. Biol. Chem.* 273, 30736–30741). Finally, NEMO (also termed IKKγ) contains three a-helical regions including a leucine zipper, interacts preferentially with IKK2 and is required for activation of the heterodimeric kinase complex perhaps by bringing other proteins into the signalsome complex (Yamaoka, S., Courtois, G., Bessia, C., Whiteside, S. T., Weil, R., Agou, F., Kirk, H. E., Kay, R. J., and Ireal, A. (1998) *Cell* 93, 1231–1240; Rothwarf, D. M., Zandi, E., Natoli, G., Karin, M. (1998) *Nature* 395, 297; Mercurio, F., Murray, B. W., Shevchenko, A., Bennet, B. L., Young, D. B., Li, J. W., Pascual, G., Motiwala, A., Zhu, H., Mann, M and Manning, A. M. (1999) *Mol. Cell. Biol.* 2, 1526–1538).

The kinase activities of IKK1 and IKK2 are regulated by phosphorylation and require an intact leucine zipper (LZ) for dimerization as well as an intact helix-loop-helix (HLH) domain, which can exert a positive regulatory effect on kinase activity even when it is expressed in trans with the remainder of the IKK protein (Regnier, C., Song, H., Gao, X., Goeddel, D., Cao, Z. and Rothe, M. (1997) *Cell* 90, 373–383; DiDonato, J. A., Hayakawa, M., Rothwarf, D. M., Zandi, E. and Karin, M. (1997) *Nature* 388, 548–554; Mercurio, F., Zhu, H., Murray, B. W., Shevchenko, A., Bennett, B. L., Li, J. W., Young, D. B., Barbosa, M., Mann, M., Manning, A. and Roa, A. (1997) *Science* 278, 860–866; Zandi, E. Rothwarf, D. M., Delhase, M., Hayadawa, M and Karin, M. (1997) *Cell* 91, 243–252; Woronicz, J. D., Gao, X., Cao, Z., Rothe, M. and Goeddel, D. V. (1997) *Science* 278, 866–869; Dehase, M., Hayakawa, M., Chen, Y., and Karin, M. (1999) *Science* 284, 309–313). Both IKK subunits contain a canonical MAPKK activation loop motif near the N-terminus which is the target for phosphorylation and activation of kinase activity by MAP3Ks such as NIK and MEKK1, although the physiologic regulation by these two upstream kinases awaits further characterization (Zandi, E., and Karin, M. (1999) *Mol. Cell. Biol.* 19, 4547–4551; Karin, M. (1999) *J. Biol. Chem.* 274, 27339–27342; Karin, M., and Delhase, M. (1998) *Proc. Natl. Acad. Sci. USA* 95, 9067–9069). Finally, phosphorylation of serines in the C-terminus of IKK2 results in a decrease in IKK activity and it is postulated to be responsible for the transient kinase activity seen after stimulation of cells with an agonist (Dehase, M., Hayakawa, M., Chen, Y., and Karin, M. (1999) *Science* 284, 309–313).

IKK2 demonstrates a more potent kinase activity compared to IKK1 using IκBα or IκBβ as a substrate (Mercurio, F., Zhu, H., Murray, B. W., Shevchenko, A., Bennett, B. L., Li, J. W., Young, D. B., Barbosa, M., Mann, M., Manning, A. and Roa, A. (1997) *Science* 278, 860–866; Zandi, E. Rothwarf, D. M., Delhase, M., Hayadawa, M and Karin, M. (1997) *Cell* 91, 243–252; Woronicz, J. D., Gao, X., Cao, Z., Rothe, M. and Goeddel, D. V. (1997) *Science* 278, 866–869; Dehase, M., Hayakawa, M., Chen, Y., and Karin, M. (1999) *Science* 284, 309–313). Mutations of the phospho-acceptor serine residues within the MAPKK activation loop alters IKK2 kinase activity; the serine to alanine substitutions result in decreased kinase activity whereas the serine to glutamic acid substitutions result in a constitutively active kinase. Similar alanine mutations in IKK1 do not result in a decreased stimulation of total IKK activity in response to TNFα or IL1β (Dehase, M., Hayakawa, M., Chen, Y., and Karin, M. (1999) *Science* 284, 309–313). IKK2 being the dominant kinase activity within the IKK complex is further supported by the analysis of fibroblasts from mice deficient in IKK1 or IKK2. Fibroblasts lacking IKK1 retain full IKK activity in response to cytokines and could activate NF-κB. In contrast, fibroblasts lacking IKK2 do not exhibit IKK activity when stimulated with cytokines nor do they activate NF-κB. Furthermore, the phenotypes of each IKK knock out is unique with IKK1 deficiency resulting in skin and skeletal defects and IKK2 knock out being embryonic lethal due to hepatocyte apoptosis (Li, Q., Antwerp, D. V., Mercurio, F., Lee, K., and Verma, I. M. (1999) *Science* 284, 321–325; Takeda, K., Tekeuchi, O., Tsujimura, T., Itami, S., Adachi, O., Kawai, T., Sanjo, H., Yoshikawa, K., Terada, N, and Akira, S. (1999) *Science* 284, 313–316; Hu, Y., Baud, V., Delhase, M., Zhang, P., Deerinck, T., Ellisman, M., Johnson, R., and Karin, M. (1999) *Science* 284, 315–320; Li, Q., Lu, Q., Hwang, J. Y., Buscher, D., Lee, K., Izpisua-Belmonte, J. C., and Verma, I. M. (1999) *Gene and Development* 13, 1322–1328; Tanaka, M., Fuentes, M. E., Yamaguchi, K., Durnin, M. H., Dalrymple, S. A., Hardy, K. L., and Goeddel, D. V. (1999) *Immunity* 10, 421–429).

It is well-known that NF-κB plays a key role in the regulated expression of a large number of pro-inflammatory mediators including cytokines such as IL-6 and IL-8, cell adhesion molecules, such as ICAM and VCAM, and inducible nitric oxide synthase (iNOS). Such mediators are known to play a role in the recruitment of leukocytes at sites of inflammation and in the case of iNOS, may lead to organ destruction in some inflammatory and autoimmune diseases. The importance of NF-κB in inflammatory disorders is further strengthened by studies of airway inflammation including asthma in which NF-κB has been shown to be activated. This activation may underlie the increased cytokine production and leukocyte infiltration characteristic of these disorders. In addition, inhaled steroids are known to reduce airway hyper responsiveness and suppress the inflammatory response in asthmatic airways. In light of the recent findings with regard to glucocorticoid inhibition of NF-κB, one may speculate that these effects are mediated through an inhibition of NF-κB. Further evidence for a role of NF-κB in inflammatory disorders comes from studies of rheumatoid synovium. Although NF-κB is normally present as an inactive cytoplasmic complex, recent immunohistochemical studies have indicated that NF-κB is present in the nuclei, and hence active, in the cells comprising rheumatoid synovium. Furthermore, NF-κB has been shown to be activated in human synovial cells in response to stimulation with TNF-α. Such a distribution may be the underlying mechanism for the increased cytokine and eicosanoid production characteristic of this tissue. See Roshak, A. K., et al., *J. Biol. Chem.*, 271, 31496–31501 (1996). The NF-κB/Rel and IκB proteins are also likely to play a key role in neoplastic transformation. Family members are associated with cell transformation in vitro and in vivo because of overexpression, gene amplification, gene rearrangements, or translocations. In addition, rearrangement and/or amplification of the genes encoding these proteins are seen in 20–25% of certain human lymphoid tumors. In addition, a role for NF-κB in the regulation of apoptosis has been reported strengthening the role of this transcription factor in the control of cell proliferation.

The NF-κB/Rel and IκB proteins are also likely to play a key role in neoplastic transformation. Family members are associated with cell transformation in vitro and in vivo because of overexpression, gene amplification, gene rearrangements, or translocations (Gilmore T D, *Trends Genet* 7:318–322, 1991; Gillmore T D, *Oncogene* 18:6925–6937, 1999; Rayet B. et al., *Oncogene* 18: 6938–6947, 1991). In addition, rearrangement and/or amplification of the genes encoding these proteins are seen in 20–25% of certain human lymphoid tumors. In addition, a role for NF-κB in the regulation of apoptosis, cell cycle progression, invasion, and metastasis has been reported (Bours V. et al., *Biochemical Pharmacology* 60:1085–1090, 2000) strengthening the role of this transcription factor in the control of cell proliferation. The inhibition of NF-κB has been shown to potentiate TNF- and cancer therapy through increased apoptosis (Wang C-Y et al., *Science* 274:784–787, 1996; Wang C-Y et al., *Nat Med* 5:412–417, 1999). It has also been shown that human T-cell leukemia virus type 1 (HTLV 1) infected cells (the etiological agent of an aggressive malignancy of activated $CD4^+$ T lymphocytes), IKKα and IKKβ are expressed constitutively, which normally function in a transient manner (Chu Z-L et al., *J of Biological Chemistry* 273:15891–15894, 1998). The HTLV1 transforming and transactivating protein (Tax) has been shown to bind MEKK1 and increases the activity of IKKβ, to enhance phosphorylation of serine residues in IκBα that lead to its degradation.

Pyrazoles have been described for use in the treatment of inflammation. U.S. Pat. No. 5,134,142 to Matsuo et al describes 1,5-diaryl pyrazoles, and specifically, 1-(4-fluorophenyl)-5-[4-(methylsulfonyl)phenyl]-3-trifluoromethyl pyrazole, as having anti-inflammatory activity.

U.S. Pat. No. 3,940,418 to R. Hamilton describes tricyclic 4,5-dihydrobenz[g]indazoles as antiinflammatory agents. In addition, R. Hamilton [*J. Heterocyclic Chem.*, 13, 545 (1976)] describes tricyclic 4,5-dihydrobenz[g]indazoles as antiinflammatory agents. U.S. Pat. No. 5,134,155 describes fused tricyclic pyrazoles having a saturated ring bridging the pyrazole and a phenyl radical as HMG-CoA reductase inhibitors. European publication EP 477,049, published Mar. 25, 1992, describes [4,5-dihydro-1-phenyl-1H-benz[g] indazol-3-yl]amides as having antipsychotic activity. European publication EP 347,773, published Dec. 27, 1989, describes [4,5-dihydro-1-phenyl-1H-benz[g]indazol-3-yl] propanamides as immunostimulants. M. Hashem et al [*J. Med. Chem.*, 19, 229 (1976)] describes fused tricyclic pyrazoles, having a saturated ring bridging the pyrazole and a phenyl radical, as antibiotics.

Certain substituted pyrazolyl-benzenesulfonamides have been described in the literature as synthetic intermediates. Specifically, 4-[5-(4-chlorophenyl)-3-phenyl-1H-pyrazol-1-yl]benzenesulfonamide has been prepared from a pyrazoline compound as an intermediate for compounds having hypoglycemic activity [R. Soliman et al, *J. Pharm. Sci.*, 76, 626 (1987)]. 4-[5-[2-(4-Bromophenyl)-2H-1,2,3-triazol-4-yl]-3-methyl-1H-pyrazol-1-yl]benzenesulfonamide has been prepared from a pyrazoline compound and described as potentially having hypoglycemic activity [H. Mokhtar, *Pak. J. Sci. Ind. Res.*, 31, 762 (1988)]. Similarly, 4-[4-bromo-5-[2-(4-chlorophenyl)-2H-1,2,3-triazol-4-yl]-3-methyl-1H-pyrazol-1-yl]benzenesulfonamide has been prepared [H. Mokhtar et al, *Pak. J. Sci. Ind. Res.*, 34, 9 (1991)].

The phytotoxicity of pyrazole derivatives is described [M. Cocco et al, *Il. Farmaco-Ed. Sci.*, 40, 272 (1985)], specifically for 1-[4-(aminosulfonyl)phenyl]-5-phenyl-1H-pyrazole-3,4-dicarboxylic acid.

The use of styryl pyrazole esters for antidiabetes drugs is described [H. Mokhtar et al, *Pharmazie*, 33, 649–651 (1978)]. The use of styryl pyrazole carboxylic acids for antidiabetes drugs is described [R. Soliman et al, *Pharmazie*, 33, 184–5 (1978)]. The use of 4-[3,4,5-trisubstituted-pyrazol-1-yl]benzenesulfonamides as intermediates for sulfonylurea anti-diabetes agents is described, and specifically, 1-[4-(aminosulfonyl)phenyl]-3-methyl-5-phenyl-1H-pyrazole-4-carboxylic acid [R. Soliman et al, *J. Pharm. Sci.*, 72, 1004 (1983)]. A series of 4-[3-substituted methyl-5-phenyl-1H-pyrazol-1-yl]benzenesulfonamides has been prepared as intermediates for anti-diabetes agents, and more specifically, 4-[3-methyl-5-phenyl-1H-pyrazol-1-yl] benzenesulfonamide [H. Feid-Allah, *Pharmazie*, 36, 754 (1981)]. In addition, 1-(4-[aminosulfonyl]phenyl)-5-phenylpyrazole-3-carboxylic acid has been prepared from the above described 4-[3-methyl-5-phenyl-1H-pyrazol-1-yl] benzenesulfonamide compound [R. Soliman et al, *J. Pharm. Sci.*, 70, 602 (1981)].

WO 00/27822 discloses tricyclic pyrazole derivatives, WO 00/59901 discloses dihydroindeno pyrazoles, WO 95/15315 discloses diphenyl pyrazole compounds, WO 95/15317 discloses triphenyl pyrazole compounds, WO 95/15318 discloses tri-substituted pyrazole compounds, and WO 96/09293 discloses benz[g]indazolyl derivatives. WO 95/15316 discloses substituted pyrazolyl benzenesulfamide derivatives.

DETAILED DESCRIPTION OF THE INVENTION

A class of compounds, which are useful in treating cancer, inflammation, and inflammation related disorders, is defined by Formula I:

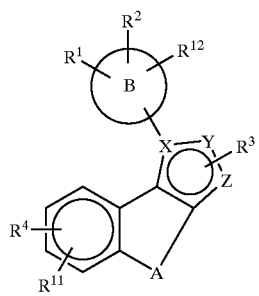

wherein

A is $(CH_2)_m$—$CR^{15}$=$CR^{16}$—$(CH_2)_m$ m is independently selected from 0, 1, or 2;

B is a 5 or 6 membered heteroaryl, aryl, saturated or unsaturated heterocyclic wherein said aryl, heteroaryl, or heterocyclic are optionally substituted with $R^1$, $R^2$, and $R^{12}$;

X is selected from the group consisting of: N and C;

Y and Z are independently selected from the group consisting of: N, CH, $CR^3$, S, and O;

$R^1$ is selected from the group consisting of: hydrido, halogen, alkyl, aryl, heteroaryl, alkenyl, alkynyl, haloalkyl, CN, $NO_2$, $OR^5$, $OCOOR^5$, $CO_2R^7$, $CON(R^6)$ $R^7$, $COR^6$, $SR^6$, $SOR^6$, $SO_2R^6$, $NR^6R^7$, $NR^6COR^7$, $NR^6CONHR^7$, $NR^6SO_2NHR^7$, and $SO_2N(R^6)R^7$ wherein $R^6$ and $R^7$ may be taken together to form a 3–7 membered carbocyclic ring having 1 to 3 substituted or unsubstituted heteroatoms selected from the group consisting of: S, SO, $SO_2$, O, and $NR^6$; wherein said alkenyl, alkynyl, alkyl, aryl, heteroaryl or $OR^5$ are optional substituted with, hydrido, halogen, alkyl, hydroxyalkyl, aryl, heteroaryl, haloalkyl, $COCF_3$, CN, $NO_2$, $OR^5$, $OCOOR^5$, $CO_2R^7$, $CON(R^6)R^7$, $COR^6$, $SR^6$, $SOR^6$, $SO_2R^6$, $NR^6R^7$, $NR^6COR^7$, $NR^6CONHR^7$, $NR^6SO_2R^7$, $NR^6SO_2NHR^7$, and $SO_2N(R^6)R^7$ wherein $R^6$ and $R^7$ may be taken together to form a 3–7 membered carbocyclic ring having 1 to 3 substituted or unsubstituted heteroatoms selected from the group consisting of: S, SO, $SO_2$, O, and $NR^6$;

$R^2$ is selected from the group consisting of: halogen, hydrido, hydroxyalkyl, alkyl, $OR^6$, CN, $NO_2$, $SR^6$, $NHR^6$, $CON(R^6)R^7$, $NHCONHR^6$, $CO_2H$, and haloalkyl;

$R^1$ and $R^2$ may be taken together to form a 5 to 7 membered saturated or unsaturated carbocyclic ring optionally containing 0 to 3 heteroatoms selected from the group consisting of N, O, or S, and wherein said ring is optionally substituted with $R^1$;

$R^3$ is selected from the group consisting of: substituted or unsubstituted amidine, alkylamino, aminoalkyl, $CONHR^7$, $NH_2$, $NHCOR^6$, and $CH_2NHCOR^6$;

$R^4$ is selected from the group consisting of: halogen, alkylsulfinyl, alkylsulfonyl, cyano, alkoxycarbonyl, alkyl, haloalkyl, hydrido, hydroxyalkyl, haloalkoxy, heterocyclic, nitro, acylamino, aryl, heteroaryl, and alkenyl, $OR^{13}$, $SR^8$, $SO_2N(R^8)R^{8'}$, $NHR^9$, $NHCOR^9$, $NR^9COR^9$, $NHCO(OR^9)$, $NR^9CO(OR^9)$, $NR^8SO_2R^{10}$, $NHSO_2N(R^{10})R^{10'}$, $NR^6CON(R^{10})R^{10'}$, $COR^9$, $CO_2R^8$, $CON(R^8)R^{8'}$, wherein $R^8$ and $R^{8'}$ may be taken together to form a 3–7 membered carbocyclic ring having 1 to 3 substituted or unsubstituted heteroatoms selected from S, SO, $SO_2$, O, N, and $NR^6$, and wherein $R^{10}$ and $R^{10'}$ may be taken together to form a 3–7 membered carbocyclic ring having 1 to 3 substituted or unsubstituted heteroatoms selected from S, SO, $SO_2$, O, N, and $NR^6$ wherein said aryl, heterocyclic, heteroaryl, or alkenyl are optionally substituted with $R^9$;

$R^5$ is selected from the group consisting of: hydrido, alkyl, aryl, arylalkyl, heteroaryl, heterocyclicalkyl, and heteroarylalkyl, wherein aryl, alkyl, arylalkyl, heteroaryl, heterocyclicalkyl, or heteroarylalkyl are optionally substituted with one or more radicals selected from the group consisting of $OR^{14}$, $N(R^{14})R^{14'}$, and glycols;

$R^6$ is independently selected from the group consisting of: hydrido, aryl, heteroaryl, lower alkyl, haloalkyl, alkenyl, alkynyl, hydroxyalkyl, aminoalkyl, alkylaminoalkyl, alkoxy, alkoxyalkyl, heterocyclicalkyl, and heterocyclic;

$R^7$ is independently selected from the group consisting of: hydrido, aryl, heteroaryl, lower alkyl, haloalkyl, alkenyl, alkynyl, hydroxyalkyl, aminoalkyl, alkylaminoalkyl, alkoxy, alkoxyalkyl, heterocyclicalkyl, and heterocyclic;

$R^8$ is independently selected from the group consisting of: hydrido, aryl, heteroaryl, arylalkyl, heterocyclic, haloalkyl, arylalkylamino, alkylaminoalkyl, dialkylaminoalkyl, alkyl, alkenyl, alkynyl, heteroarylalkyl, and heterocyclicalkyl;

$R^{8'}$ is independently selected from the group consisting of: hydrido, aryl, heteroaryl, arylalkyl, heterocyclic, haloalkyl, arylalkylamino, alkylaminoalkyl, dialkylaminoalkyl, alkyl, alkenyl, alkynyl, heteroarylalkyl, and heterocyclicalkyl;

$R^9$ is independently selected from the group consisting of: hydrido, lower alkyl, aryl, heteroaryl, arylalkyl, heterocyclic, cycloalkyl, heterocyclicalkyl, haloalkyl, arylalkylamino, amino, aminoalkyl, aminoacyl, nitro, azido, and heteroarylalkyl, wherein alkyl, aryl, heteroaryl, aminoalkyl, or arylalkyl are optionally substituted with one or more radical selected from the group consisting of: alkylsulfonamide, sulfamyl, alkyl, alkylthio, alkylsulfinyl, alkylsulfonyl, alkylamino, aminoalkyl, alkylaminoalkyl, alkoxy, halogen, acyloxy, oxy, formyl, haloalkyl, cyano, haloalkoxy, acyl, carboxyl, hydroxy, hydroxyalkyloxy, phenoxy, nitro, azido, benzyloxy, dialkylaminoacyl, thioalkyl, aminoacyloxy, thiocyanate, isothiocyanate, alkyldioxy, hydroxyalkyl, alkylamino, alkyloxycarbonyl, alkoxyalkyl, alkenylamino, alkynylamino, alkenyl, alkynyl, dialkylaminoalkyloxy, and heterocyclic optionally substituted with alkyl, alkylamino, aminoalkyl, hydroxyalkyl, and alkylaminoalkyl;

$R^{10}$ is independently selected from the group consisting of: hydrido, lower alkyl, heteroaryl, heterocyclic, haloalkyl, arylalkylamino, heteroarylalkyl, aryl, and arylalkyl, wherein aryl, heteroaryl, heterocyclic, or arylalkyl are optionally substituted with one or more radical selected from alkyl, alkoxy, halogen, haloalkyl, cyano, haloalkoxy, acyl, carboxyl, hydroxy, hydroxyalkyloxy, phenoxy, benzyloxy, dialkylaminoalkyloxy, and heterocyclic;

$R^{10'}$ is independently selected from the group consisting of: hydrido, lower alkyl, heteroaryl, heterocyclic, haloalkyl, arylalkylamino, heteroarylalkyl, aryl, and arylalkyl, wherein aryl, heteroaryl, heterocyclic, or arylalkyl are optionally substituted with one or more radical selected from alkyl, alkoxy, halogen, haloalkyl, cyano, haloalkoxy, acyl, carboxyl, hydroxy, hydroxyalkyloxy, phenoxy, benzyloxy, dialkylaminoalkyloxy, and heterocyclic; and $R^{11}$ is selected from the group consisting of: hydrido, halogen, haloalkyl, CN, $CO_2R^5$, lower alkyl, lower alkenyl, lower alkynyl, alkoxy, and $CONH_2$;

$R^{12}$ is selected from the group consisting of: hydrido, halogen, alkyl, and alkoxy;

$R^{13}$ is selected from the group consisting of: hydrido, alkyl, aryl, arylalkyl, heteroaryl, heterocyclicalkyl, and heteroarylalkyl, wherein aryl, alkyl, arylalkyl, heteroaryl, heterocyclicalkyl, or heteroarylalkyl are optionally substituted with one or more radicals selected from the group consisting of $OR^{14}$, $N(R^{14})R^{14'}$, and glycols;

$R^{14}$ is independently selected from the group consisting of hydrido, and lower alkyl; and $R^{14'}$ is independently selected from the group consisting of hydrido, and lower alkyl;

$R^{15}$ is selected from the group consisting of: hydrido, halogen, alkyl, cycloalkyl, aryl, haloalkyl, heteroaryl, heterocyclic, alkylalkene, alkylalkyne, hydroxy, hydroxyalkyl, alkylhydroxy, amino, aminoalkyl, alkylamino, alkylaminoalkyl, alkylhydroxyalkyl, nitro, cyano, alkylthio, alkylsulfinyl, alkylsulfonyl; wherein aryl or arylalkyl are optionally substituted with one or more radical selected from alkyl, alkoxy, halo, haloalkyl, cyano, haloalkoxy, acyl, carboxyl, hydroxy, hydroxyalkyloxy, phenoxy, benzyloxy, dialkylaminoalkyloxy, heterocyclic; and $R^{16}$ is selected from the group consisting of: hydrido, halogen, alkyl, cycloalkyl, aryl, haloalkyl, heteroaryl, heterocyclic, alkylalkene, alkylalkyne, hydroxy, hydroxyalkyl, alkylhydroxy, amino, aminoalkyl, alkylamino, alkylaminoalkyl, alkylhydroxyalkyl, nitro, cyano, alkylthio, alkylsulfinyl, alkylsulfonyl; wherein aryl or arylalkyl are optionally substituted with one or more radical selected from alkyl, alkoxy, halo, haloalkyl, cyano, haloalkoxy, acyl, carboxyl, hydroxy, hydroxyalkyloxy, phenoxy, benzyloxy, dialkylaminoalkyloxy, heterocyclic; wherein $R^{15}$ and $R^{16}$ may be taken together to form a 5 to 7 membered saturated or unsaturated carbocyclic ring optionally containing 0 to 3 heteroatoms selected from the group consisting of N, O, or S, and wherein said ring is optionally substituted with $R^1$;

or isomers, tautomers, carriers, esters, prodrugs, pharmaceutically acceptable salts thereof.

Another class of compounds is defined by formula II

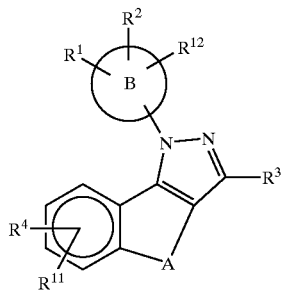

wherein

A is $(CH_2)_m$—$CR^{15}$=$CR^{16}$—$(CH_2)_m$ m is independently selected from 0, 1, or 2;

B is a 5 or 6 membered heteroaryl, aryl, saturated or unsaturated heterocyclic wherein said aryl, heteroaryl, or heterocyclic are optionally substituted with $R^1$, $R^2$, and $R^{12}$;

$R^1$ is selected from the group consisting of: hydrido, halogen, alkyl, aryl, heteroaryl, alkenyl, alkynyl, haloalkyl, CN, $NO_2$, $OR^5$, $OCOOR^5$, $CO_2R^7$, $CON(R^6)R^7$, $COR^6$, $SR^6$, $SOR^6$, $SO_2R^6$, $NR^6R^7$, $NR^6COR^7$, $NR^6CONHR^7$, $NR^6SO_2R^7$, $NR^6SO_2NHR^7$, and $SO_2N(R^6)R^7$ wherein $R^6$ and $R^7$ may be taken together to form a 3–7 membered carbocyclic ring having 1 to 3 substituted or unsubstituted heteroatoms selected from the group consisting of: S, SO, $SO_2$, O, and $NR^6$; wherein said alkenyl, alkynyl, alkyl, aryl, heteroaryl or $OR^5$ are optional substituted with, hydrido, halogen, alkyl, hydroxyalkyl, aryl, heteroaryl, haloalkyl, $COCF_3$, CN, $NO_2$, $OR^5$, $OCOOR^5$, $CO_2R^7$, $CON(R^6)R^7$, $COR^6$, $SR^6$, $SOR^6$, $SO_2R^6$, $NR^6R^7$, $NR^6COR^7$, $NR^6CONHR^7$, $NR^6SO_2R^7$, $NR^6SO_2NHR^7$, and $SO_2N(R^6)R^7$ wherein $R^6$ and $R^7$ may be taken together to form a 3–7 membered carbocyclic ring having 1 to 3 substituted or unsubstituted heteroatoms selected from the group consisting of: S, SO, $SO_2$, O, and $NR^6$;

$R^2$ is selected from the group consisting of: halogen, hydrido, hydroxyalkyl, alkyl, $OR^6$, CN, $NO_2$, $SR^6$, $NHR^6$, $CON(R^6)R^7$, $NHCONHR^6$, $CO_2H$, and haloalkyl; $R^1$ and $R^2$ may be taken together to form a 5 to 7 membered saturated or unsaturated carbocyclic ring optionally containing 0 to 3 heteroatoms selected from the group consisting of N, O, or S, and wherein said ring is optionally substituted with $R^1$;

$R^3$ is selected from the group consisting of: substituted or unsubstituted amidine, alkylamino, aminoalkyl, $CONHR^7$, $NH_2$, $NHCOR^6$, and $CH_2NHCOR^6$;

$R^4$ is selected from the group consisting of: halogen, alkylsulfinyl, alkylsulfonyl, cyano, alkoxycarbonyl, alkyl, haloalkyl, hydrido, hydroxyalkyl, haloalkoxy, heterocyclic, nitro, acylamino, aryl, heteroaryl, and alkenyl, $OR^{13}$, $SR^8$, $SO_2N(R^8)R^{8'}$, $NHR^9$, $NHCOR^9$, $NR^9COR^9$, $NHCO(OR^9)$, $NR^9CO(OR^9)$, $NR^8SO_2R^{10}$, $NHSO_2N(R^{10})R^{10'}$, $NR^6CON(R^{10})R^{10'}$, $COR^9$, $CO_2R^8$, $CON(R^8)R^{8'}$, wherein $R^8$ and $R^{8'}$ may be taken together to form a 3–7 membered carbocyclic ring having 1 to 3 substituted or unsubstituted heteroatoms selected from S, SO, $SO_2$, O, N, and $NR^6$, and wherein $R^{10}$ and $R^{10'}$ may be taken together to form a 3–7 membered carbocyclic ring having 1 to 3 substituted or unsubstituted heteroatoms selected from S, SO, $SO_2$, O, N, and $NR^6$ wherein said aryl, heterocyclic, heteroaryl, or alkenyl are optionally substituted with $R^9$;

$R^5$ is selected from the group consisting of: hydrido, alkyl, aryl, arylalkyl, heteroaryl, heterocyclicalkyl, and heteroarylalkyl, wherein aryl, alkyl, arylalkyl, heteroaryl, heterocyclicalkyl, or heteroarylalkyl are optionally substituted with one or more radicals selected from the group consisting of $OR^{14}$, $N(R^{14})R^{14'}$, and glycols;

$R^6$ is independently selected from the group consisting of: hydrido, aryl, heteroaryl, lower alkyl, haloalkyl, alkenyl, alkynyl, hydroxyalkyl, aminoalkyl, alkylaminoalkyl, alkoxy, alkoxyalkyl, heterocyclicalkyl, and heterocyclic;

$R^7$ is independently selected from the group consisting of: hydrido, aryl, heteroaryl, lower alkyl, haloalkyl, alkenyl, alkynyl, hydroxyalkyl, aminoalkyl, alkylaminoalkyl, alkoxy, alkoxyalkyl, heterocyclicalkyl, and heterocyclic;

$R^8$ is independently selected from the group consisting of: hydrido, aryl, heteroaryl, arylalkyl, heterocyclic, haloalkyl, arylalkylamino, alkylaminoalkyl, dialkylaminoalkyl, alkyl, alkenyl, alkynyl, heteroarylalkyl, and heterocyclicalkyl;

$R^{8'}$ is independently selected from the group consisting of: hydrido, aryl, heteroaryl, arylalkyl, heterocyclic, haloalkyl, arylalkylamino, alkylaminoalkyl, dialkylaminoalkyl, alkyl, alkenyl, alkynyl, heteroarylalkyl, and heterocyclicalkyl;

$R^9$ is independently selected from the group consisting of: hydrido, lower alkyl, aryl, heteroaryl, arylalkyl, heterocyclic, cycloalkyl, heterocyclicalkyl, haloalkyl, arylalkylamino, amino, aminoalkyl, aminoacyl, nitro, azido, and heteroarylalkyl, wherein alkyl, aryl, heteroaryl, aminoalkyl, or arylalkyl are optionally substituted with one or more radical selected from the group consisting of: alkylsulfonamide, sulfamyl, alkyl, alkylthio, alkylsulfinyl, alkylsulfonyl, alkylamino, aminoalkyl, alkylaminoalkyl, alkoxy, halogen, acyloxy, oxy, formyl, haloalkyl, cyano, haloalkoxy, acyl, carboxyl, hydroxy, hydroxyalkyloxy, phenoxy, nitro, azido, benzyloxy, dialkylaminoacyl, thioalkyl, aminoacyloxy, thiocyanate, isothiocyanate, alkyldioxy, hydroxyalkyl, alkylamino, alkyloxycarbonyl, alkoxyalkyl, alkenylamino, alkynylamino, alkenyl, alkynyl, dialkylaminoalkyloxy, and heterocyclic optionally substituted with alkyl, alkylamino, aminoalkyl, hydroxyalkyl, and alkylaminoalkyl;

$R^{10}$ is independently selected from the group consisting of: hydrido, lower alkyl, heteroaryl, heterocyclic, haloalkyl, arylalkylamino, heteroarylalkyl, aryl, and arylalkyl, wherein aryl, heteroaryl, heterocyclic, or arylalkyl are optionally substituted with one or more radical selected from alkyl, alkoxy, halogen, haloalkyl, cyano, haloalkoxy, acyl, carboxyl, hydroxy, hydroxyalkyloxy, phenoxy, benzyloxy, dialkylaminoalkyloxy, and heterocyclic;

$R^{10'}$ is independently selected from the group consisting of: hydrido, lower alkyl, heteroaryl, heterocyclic, haloalkyl, arylalkylamino, heteroarylalkyl, aryl, and arylalkyl, wherein aryl, heteroaryl, heterocyclic, or arylalkyl are optionally substituted with one or more radical selected from alkyl, alkoxy, halogen, haloalkyl, cyano, haloalkoxy, acyl, carboxyl, hydroxy, hydroxyalkyloxy, phenoxy, benzyloxy, dialkylaminoalkyloxy, and heterocyclic;

$R^{11}$ is selected from the group consisting of: hydrido, halogen, haloalkyl, CN, $CO_2R^5$, lower alkyl, lower alkenyl, lower alkynyl, alkoxy, and $CONH_2$;

$R^{12}$ is selected from the group consisting of: hydrido, halogen, alkyl, and alkoxy;

$R^{13}$ is selected from the group consisting of: hydrido, alkyl, aryl, arylalkyl, heteroaryl, heterocyclicalkyl, and heteroarylalkyl, wherein aryl, alkyl, arylalkyl, heteroaryl, heterocyclicalkyl, or heteroarylalkyl are optionally substituted with one or more radicals selected from the group consisting of $OR^{14}$, $N(R^{14})R^{14'}$, and glycols;

$R^{14}$ is independently selected from the group consisting of hydrido, and lower alkyl; and $R^{14'}$ is independently selected from the group consisting of hydrido, and lower alkyl;

$R^{15}$ is selected from the group consisting of: hydrido, halogen, alkyl, cycloalkyl, aryl, haloalkyl, heteroaryl, heterocyclic, alkylalkene, alkylalkyne, hydroxy, hydroxyalkyl, alkylhydroxy, amino, aminoalkyl, alkylamino, alkylaminoalkyl, alkylhydroxyalkyl, nitro, cyano, alkylthio, alkylsulfinyl, alkylsulfonyl; wherein aryl or arylalkyl are optionally substituted with one or more radical selected from alkyl, alkoxy, halo, haloalkyl, cyano, haloalkoxy, acyl, carboxyl, hydroxy, hydroxyalkyloxy, phenoxy, benzyloxy, dialkylaminoalkyloxy, heterocyclic; and $R^{16}$ is selected from the group consisting of: hydrido, halogen, alkyl, cycloalkyl, aryl, haloalkyl, heteroaryl, heterocyclic, alkylalkene, alkylalkyne, hydroxy, hydroxyalkyl, alkylhydroxy, amino, aminoalkyl, alkylamino, alkylaminoalkyl, alkylhydroxyalkyl, nitro, cyano, alkylthio, alkylsulfinyl, alkylsulfonyl; wherein aryl or arylalkyl are optionally substituted with one or more radical selected from alkyl, alkoxy, halo, haloalkyl, cyano, haloalkoxy, acyl, carboxyl, hydroxy, hydroxyalkyloxy, phenoxy, benzyloxy, dialkylaminoalkyloxy, heterocyclic; wherein $R^{15}$ and $R^{16}$ may be taken together to form a 5 to 7 membered saturated or unsaturated carbocyclic ring optionally containing 0 to 3 heteroatoms selected from the group consisting of N, O, or S, and wherein said ring is optionally substituted with $R^1$;

or isomers, tautomers, carriers, esters, prodrugs, pharmaceutically acceptable salts thereof.

Definitions

The present invention includes the use of all hydrates, solvates, complexes and prodrugs of the compounds of this invention. Prodrugs are any covalently bonded compounds, which release the active parent drug according to Formula I or II in vivo. If a chiral center or another form of an isomeric center is present in a compound of the present invention all forms of such isomer or isomers, including enantiomers and diastereomers, are intended to be covered herein. Compounds containing a chiral center may be used as a racemic mixture, an enantiomerically enriched mixture, or the racemic mixture may be separated using well-known techniques and an individual enantiomer may be used alone. In cases in which compounds have unsaturated carbon-carbon double bonds, both the cis (Z) and trans (E) isomers are within the scope of this invention. In cases wherein compounds may exist in tautomeric forms, such as keto-enol tautomers, each tautomeric form is contemplated as being included within this invention whether existing in equilibrium or predominantly in one form.

The meaning of any substituent at any one occurrence in Formula I and II or any sub-formula thereof is independent of its meaning, or any other substituents meaning, at any other occurrence, unless specified otherwise.

The term "alkyl" is used, either alone or within other terms such as "haloalkyl" and "alkylsulfonyl"; it embraces linear or branched radicals having one to about twenty carbon atoms or, preferably, one to about twelve carbon atoms. More preferred alkyl radicals are "lower alkyl" radicals having one to about ten carbon atoms. Most preferred are lower alkyl radicals having one to about five carbon atoms. Examples of such radicals include methyl, ethyl, n-propyl, isopropyl, n-butyl, isobutyl, sec-butyl, tert-butyl, pentyl, isoamyl, hexyl, octyl and the, like. The term "hydrido" denotes a single hydrogen atom (H). This hydrido radical may be attached, for example, to an oxygen atom to form a hydroxyl radical or two hydrido radicals may be attached to a carbon atom to form a methylene (—$CH_2$—) radical. The term "halo" means halogens such as fluorine, chlorine, and bromine or iodine atoms. The term "haloalkyl" embraces radicals wherein any one or more of the alkyl carbon atoms is substituted with halo as defined above. Specifically embraced are monohaloalkyl, dihaloalkyl, and polyhaloalkyl radicals. A monohaloalkyl radical, for one example, may have a bromo, chloro, or a fluoro atom within the radical. Dihalo radicals may have two or more of the same halo atoms or a combination of different halo radicals and polyhaloalkyl radicals may have more than two of the same halo atoms or a combination of different halo radicals. The term "hydroxyalkyl" embraces linear or branched alkyl radicals having one to about ten carbon atoms any one of which may be substituted with one or more hydroxylradicals. The terms "alkoxy" and "alkoxyalkyl" embrace linear or branched oxy-containing radicals each having alkyl portions of one to about ten carbon atoms, such as methoxy radical. The term "alkoxyalkyl" also embraces alkyl radicals having two or more alkoxy radicals attached to the alkyl radical, that is, to form monoalkoxyalkyl and dialkoxyalkyl radicals. The "alkoxy" or "alkoxyalkyl" radicals may be further substituted with one or more halo atoms, such as fluoro, chloro, or bromo, to provide "haloalkoxy" or "haloalkoxyalkyl" radicals. Examples of "alkoxy" radicals include methoxy, butoxy, and trifluoromethoxy. The term "aryl", alone or in combination, means a carbocyclic aromatic system containing one, two, or three rings wherein such rings may be attached together in a pendent manner or may be fused. The term "aryl" embraces aromatic radicals such as phenyl, naphthyl, tetrahydronapthyl, indane, and biphenyl. The term "heterocyclic" embraces saturated, partially saturated, and unsaturated heteroatom-containing ring-shaped radicals, where the heteroatoms may be selected from nitrogen, sulfur and oxygen. Examples of saturated heterocyclic radicals include pyrrolidyl and morpholinyl. The term "heteroaryl" embraces unsaturated heterocyclic radicals. Examples of unsaturated heterocyclic radicals, also termed "heteroaryl" radicals include thienyl, pyrrolyl, furyl, pyridyl, pyrimidyl, pyrazinyl, pyrazolyl, oxazolyl, isoxazolyl, imidazolyl, thiazolyl, and tetrazolyl. The term also embraces radicals where heterocyclic radicals are fused with aryl radicals. Examples of such fused bicyclic radicals include benzofuran, benzothiophene, and the like. The term "heterocyclic alkyl" embraces alkyl attached to the heterocyclic. The term "sulfonyl", whether used alone or linked to other terms such as alkylsulfonyl, denotes respectively divalent radicals —$SO_2$—. "Alkylsulfonyl", embraces alkyl radicals attached to a sulfonyl radical, where alkyl is defined as above. The term "arylsulfonyl" embraces sulfonyl radicals substituted with an aryl radical. The terms "sulfamyl" or "sulfonamidyl", whether alone or used with terms such as "N-alkylsulfamyl", "N-arylsulfamyl", "N,N-dialkylsulfamyl" and "N-alkyl-N-arylsulfamyl", denotes a sulfonyl radical substituted with an amine radical, forming a sulfonamide (—$SO_2$—$NH_2$). The terms "N-alkylsulfamyl" and "N,N-dialkylsulfamyl" denote sulfamyl radicals substituted, respectively, with one alkyl radical, a cycloalkyl ring, or two alkyl radicals. The terms "N-arylsulfamyl" and "N-alkyl-N-arylsulfamyl" denote sulfamyl radicals substituted, respectively, with one aryl radical, and one alkyl and one aryl radical. The terms "carboxy" or "carboxyl", whether used alone or with other terms, such as "carboxyalkyl", denotes —$CO_2H$. The term "carboxyalkyl" embraces radicals having a carboxyradical as defined above, attached to an alkyl radical. The term "carbonyl", whether used alone or with other terms, such as "alkylcarbonyl", denotes —(C=O)—. The term "alkylcarbonyl" embraces radicals having a carbonyl radical substituted with an alkyl radical. An example of an "alkylcarbonyl" radical is $CH_3$—(C=O)—. The term "alkylcarbonylalkyl" denotes an alkyl radical substituted with an "alkylcarbonyl" radical. The term "alkoxycarbonyl" means a radical containing an alkoxy radical, as defined above, attached via an oxygen atom to a carbonyl (C=O) radical. Examples of such "alkoxycarbonyl" radicals include $(CH_3)_3CO$—C(=O)— and —(O=)C—$OCH_3$. The term "alkoxycarbonylalkyl" embraces radicals having "alkoxycarbonyl", as defined above substituted to an alkyl radical. Examples of such "alkoxycarbonylalkyl" radicals include $(CH_3)_3COC(=O)(CH_2)_2$— and —$(CH_2)_2$(O=)$COCH_3$. The term "amido" when used by itself or with other terms such as "amidoalkyl", "N-monoalkylamido", "N-monoarylamido", "N,N-dialkylamido", "N-alkyl-N-arylamido", "N-alkyl-N-hydroxyamido" and "N-alkyl-N-hydroxyamidoalkyl", embraces a carbonyl radical substituted with an amino radical. The terms "N-alkylamido" and "N,N-dialkylamido" denote amido groups which have been substituted with one alkyl radical and with two alkyl radicals, respectively. The terms "N-monoarylamido" and "N-alkyl-N-arylamido" denote amido radicals substituted, respectively, with one aryl radical, and one alkyl and one aryl radical. The term "N-alkyl-N-hydroxyamido" embraces amido radicals substituted with a hydroxyl radical and with an alkyl radical. The term "N-alkyl-N-hydroxyamidoalkyl" embraces alkyl radicals substituted with an N-alkyl-N-hydroxyamido radical. The term "amidoalkyl" embraces alkyl radicals substituted with amido radicals. The term "aminoalkyl" embraces alkyl radicals substituted with amino radicals. The term "alkylaminoalkyl" embraces aminoalkyl radicals having the nitrogen atom substituted with an alkyl radical. The term "amidino" denotes an —C(=NH)—$NH_2$ radical. The term "cyanoamidino" denotes an —C(=N—CN)—$NH_2$ radical. The term "heterocycloalkyl" embraces heterocyclic-substituted alkyl radicals such as pyridylmethyl and thienylmethyl. The term "aralkyl" embraces aryl-substituted alkyl radicals such as benzyl, diphenylmethyl, triphenylmethyl, phenethyl, and diphenethyl. The terms benzyl and phenylmethyl are interchangeable. The term "cycloalkyl" embraces radicals having three to ten carbon atoms, such as cyclopropyl cyclobutyl, cyclopentyl, cyclohexyl, and cycloheptyl. The term "cycloalkenyl" embraces unsaturated radicals having three to ten carbon atoms, such as cylopropenyl, cyclobutenyl, cyclopentenyl, cyclohexenyl, and cycloheptenyl. The term "alkylthio" embraces radicals containing a linear or branched alkyl radical, of one to ten carbon atoms, attached to a divalent sulfur atom. An example of "alkylthio" is methylthio, ($CH_3$—S—). The term "alkylsulfinyl" embraces radicals containing a linear or branched alkyl radical, of one to ten carbon atoms, attached to a divalent —S(=O)— atom. The terms "N-alkylamino" and "N,N-dialkylamino" denote amino groups which have been substituted with one alkyl radical and with two alkyl radicals, respectively. The term "acyl", whether used alone, or within a term such as "acylamino", denotes a radical provided by the residue after removal of hydroxyl from an organic acid. The term "acylamino" embraces an amino radical substituted with an acyl group. An examples of an "acylamino" radical is acetylamino ($CH_3C(=O)$—NH—).

Compounds of Formula I and II would be useful for, but not limited to, the treatment of inflammation in a subject, and for treatment of other inflammation-associated disorders, such as, as an analgesic in the treatment of pain and headaches, or as an antipyretic for the treatment of fever. For example, compounds of Formula I and II would be useful to treat arthritis, including but not limited to rheumatoid arthritis, spondylo arthopathies, gouty arthritis, osteoarthritis, systemic lupus erythematosus, and juvenile arthritis. Such compounds of Formula I and II would be useful in the treatment of asthma, bronchitis, menstrual cramps, tendinitis, bursitis, and skin related conditions such as psoriasis, eczema, burns, and dermatitis. Compounds of Formula I and II also would be useful to treat gastrointestinal conditions such as inflammatory bowel disease, Crohn's disease, gastritis, irritable bowel syndrome, and ulcerative colitis and for the prevention of colorectal cancer. Compounds of Formula I and II would be useful in treating inflammation in such diseases as vascular diseases, migraine headaches, periarteritis nodosa, thyroiditis, aplastic anemia, Hodgkin's disease, sclerodoma, rheumatic fever, type I diabetes, myasthenia gravis, sarcoidosis, nephrotic syndrome, Behcet's syndrome, polymyositis, gingivitis, hypersensitivity, conjunctivitis, swelling occurring after injury, myocardial ischemia, and the like. The compounds are useful as antiinflammatory agents, such as for the treatment of arthritis, with the additional benefit of having significantly less harmful side effects. The compounds of formula I or II are useful as agents for treating cancer or as an anticancer agents. The compounds of formula I or II may be proapoptotic, antiapoptotic, anticell cycle progressive, antiinvasive, and antimetastatic. More specifically, the compounds of this invention are useful in the treatment of a variety of cancers including, but not limited to: carcinoma such as bladder, breast, colon, kidney, liver, lung, including small cell lung cancer, esophagus, gall-bladder, ovary, pancreas, stomach, cervix, thyroid, prostate, and skin, including squamous cell carcinoma; hematopoietic tumors of lymphoid lineage, including leukemia, acute lymphocytic leukemia, acute lymphoblastic leukemia, B-cell lymphoma, T-cell-lymphoma, Hodgkin's lymphoma, non-Hodgkin's lymphoma, hairy cell lymphoma and Burkett's lymphoma; hematopoietic tumors of myeloid lineage, including acute and chronic myclogenous leukemias, myelodysplastic syndrome and promyelocytic leukemia; tumors of mesenchymal origin, including fibrosarcoma and rhabdomyosarcoma; tumors of the central and peripheral nervous system, including astrocytoma, neuroblastoma, glioma and schwannomas; other tumors, including melanoma, seminoma, teratocarcinoma, osteosarcoma, xeroderma pigmentosum, keratoxanthoma, thyroid follicular cancer and Kaposi's sarcoma. Due to the key role of protein kinases in the regulation of cellular proliferation, these compounds are also useful in the treatment of a variety of cell proliferative disorders such as, for instance, benign prostate hyperplasia, familial adenomatosis, polyposis, neuro-fibromatosis, psoriasis, vascular smooth cell proliferation associated with atherosclerosis, pulmonary fibrosis, arthritis glomerulonephritis and post-surgical stenosis and restenosis. The compounds of formula I or II may be used as an anitviral agent. The compounds of this invention are useful as inhibitors of protein kinases. The compounds of this invention are useful as inhibitors of IKK1 and/or IKK2, IKKα/IKKβ heterodimer, TBK or IKKi. The compounds of the invention may also useful as inhibitors of other protein kinases such as, for instance, protein kinase C in different isoforms, cyclin dependent kinase (cdk), Met, PAK-4, PAK-5, ZC-1, STLK-2, DDR-2, Aurora 1, Aurora 2, Bub-1, PLK, Chk1, Chk2, HER2, raf1, MEK1, MAPK, EGF-R, PDGF-R, FGF-R, IGF-R, VEGF-R, PI3K, weel kinase, Src, Abl, Akt, ILK, MK-2, IKK-2, Cdc7, Nek, and thus be effective in the treatment of diseases associated with other protein kinases. The present invention preferably includes compounds, which selectively inhibit IKK2 over IKK1. Preferably, the compounds have an IKK2 IC50 of less than 1 $\mu$M, and have a selectivity ratio of IKK2 inhibition over IKK1 inhibition of at least 50, and more preferably of at least 100. Even more preferably, the compounds have an IKK1 IC50 of greater than 10 $\mu$M, and more preferably of greater than 100 $\mu$M. The compounds of formula may also be used to treat angiogenesis associated cardiovascular, ophthalmology and osteoporosis disorders. The compounds of the present invention may also be used for treatment of knee injury such as sport injuries.

While it is possible for an active ingredient to be administered alone as the raw chemical, it is preferable to present it as a pharmaceutical formulation. The present invention comprises a pharmaceutical composition comprising a therapeutically effective amount of a compound of the present invention in association with at least one pharmaceutically acceptable carrier, adjuvant, or diluent. The present invention also comprises a method of treating inflammation or inflammation associated disorders in a subject, the method comprising administering to the subject having such inflammation or disorders a therapeutically effective amount of a compound of the present invention. Also included in the family of compounds of the present invention are the pharmaceutically acceptable salts thereof. The term "pharmaceutically acceptable salts" embraces salts commonly used to form alkali metal salts and to form addition salts of free acids or free bases. The nature of the salt is not critical, provided that it is pharmaceutically acceptable. Suitable pharmaceutically acceptable acid addition salts of compounds of the present invention may be prepared from an inorganic acid or from an organic acid. Examples of such inorganic acids are hydrochloric, hydrobromic, hydroiodic, nitric, carbonic, sulfuric, and phosphoric acid. Appropriate organic acids may be selected from aliphatic, cycloaliphatic, aromatic, araliphatic, heterocyclic, carboxylic and sulfonic classes of organic acids, examples of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, salicyclic, salicyclic, phydroxybenzoic, phenylacetic, mandelic, embonic (pamoic), methanesulfonic, ethanesulfonic, benzenesulfonic, pantothenic, toluenesulfonic, 2-hydroxyethanesulfonic, sulfanilic, stearic, cyclohexylaminosulfonic, algenic, β-hydroxybutyric, salicyclic, galactaric and galacturonic acid. Suitable pharmaceutically acceptable base addition salts of compounds of the present invention include metallic salts made from aluminum, calcium, lithium, magnesium, potassium, sodium and zinc or organic salts made from N,N'-dibenzylethylenediamine, chloroprocaine, choline, diethanolamine, ethylenediamine, meglumine (N-methylglucamine) and procaine. All of these salts may be prepared by conventional means from the corresponding compound of the present invention by reacting, for example, the appropriate acid or base with the compound of the present invention.

Also embraced within this invention are pharmaceutical compositions comprising one or more compounds of the present invention in association with one or more non-toxic, pharmaceutically acceptable carriers and/or diluents and/or adjuvants and/or excipient (collectively referred to herein as "carrier" materials) and, if desired, other active ingredients. Accordingly, the compounds of the present invention may be used in the manufacture of a medicament. Pharmaceutical compositions of the compounds of the present invention prepared as herein before described may be formulated as solutions or lyophilized powders for parenteral administration. Powders may be reconstituted by addition of a suitable diluent or other pharmaceutically acceptable carrier prior to use. The liquid formulation may be a buffered, isotonic aqueous solution. The compounds of the present invention may be administered by any suitable route, preferably in the form of a pharmaceutical composition adapted to such a route, and in a dose effective for the treatment intended. The compounds and composition may, for example, be administered intravascularly, intraperitoneally, intravenously, subcutaneously, intramuscularly, intramedullary, orally, or topically. For oral administration, the pharmaceutical composition may be in the form of, for example, a tablet, capsule, suspension, or liquid. The active ingredient may also be administered by injection as a composition wherein, for example, normal isotonic saline solution, standard 5% dextrose in water or buffered sodium or ammonium acetate solution may be used as a suitable carrier. Such formulation is especially suitable for parenteral administration, but may also be used for oral administration or contained in a metered dose inhaler or nebulizer for insufflation. It may be desirable to add excipients such as polyvinylpyrrolidone, gelatin, hydroxy cellulose, acacia, polyethylene glycol, mannitol, sodium chloride, or sodium citrate. The pharmaceutical composition is preferably made in the form of a dosage unit containing a particular amount of the active ingredient. Examples of such dosage units are tablets or capsules. The amount of therapeutically active compound that is administered and the dosage regimen for treating a disease condition with the compounds and/or compositions of this invention depends on a variety of factors, including the age, weight, sex and medical condition of the subject, the severity of the disease, the route and frequency of administration, and the particular compound employed, and thus may vary widely. The pharmaceutical compositions may contain active ingredient in the range of about 0.1 to 2000 mg, preferably in the range of about 0.5 to 500 mg and most preferably between about 1 and 100 mg. A daily dose of about 0.01 to 100 mg/kg bodyweight, preferably between about 0.1 and about 50 mg/kg body weight and most preferably between about 1 to 20 mg/kg bodyweight, may be appropriate. The daily dose can be administered in one to four doses per day. For therapeutic purposes, the compounds of this invention are ordinarily combined with one or more adjuvants appropriate to the indicated route of administration. If administered orally, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled release formulation as may be provided in a dispersion of active compound in a sustained release material such as glyceryl monostearate, glyceryl distearate, hydroxypropylmethyl cellulose alone or with a wax. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. The pharmaceutical preparations are made following the conventional techniques of pharmacy involving milling, mixing, granulating, and compressing, when necessary, for tablet forms; or milling, mixing and filling for hard gelatin capsule forms. When a liquid carrier is used, the preparation will be in the form of a syrup, elixir, emulsion, or an aqueous or non-aqueous suspension. Such a liquid formulation may be administered orally or filled into a soft gelatin capsule. For rectal administration, the compounds of the present invention may also be combined with excipients such as cocoa butter, glycerin, gelatin, or polyethylene glycols and molded into a suppository. The methods of the present invention include topical administration of the compounds of the present invention. By topical administration is meant non-systemic administration, including the application of a compound of the invention externally to the epidermis, to the buccal cavity and instillation of such a compound into the ear, eye, and nose, wherein the compound does not significantly enter the blood stream. By systemic administration is meant oral, intravenous, intraperitoneal, and intramuscular administration. The amount of a compound of the present invention (hereinafter referred to as the active ingredient) required for therapeutic or prophylactic effect upon topical administration will, of course, vary with the compound chosen, the nature and severity of the condition being treated and the animal undergoing treatment, and is ultimately at the discretion of the physician.

The topical formulations of the present invention, both for veterinary and for human medical use, comprise an active ingredient together with one or more acceptable carriers therefore, and optionally any other therapeutic ingredients. The carrier must be "acceptable" in the sense of being compatible with the other ingredients of the formulation and not deleterious to the recipient thereof. Formulations suitable for topical administration include liquid or semi-liquid preparations suitable for penetration through the skin to the site of where treatment is required such as: liniments, lotions, creams, ointments or pastes, and drops suitable for administration to the eye, ear or nose. The active ingredient may comprise, for topical administration, from 0.01 to 5.0 wt %. of the formulation.

Drops according to the present invention may comprise sterile aqueous or oily solutions or suspensions and may be prepared by dissolving the active ingredient in a suitable aqueous solution of a bactericidal and/or fungicidal agent and/or any other suitable preservative, and preferably including a surface active agent. The resulting solution may then be clarified by filtration, transferred to a suitable container, which is then sealed and sterilized by autoclaving, or maintaining at 90–100° C. for half an hour. Alternatively, the solution may be sterilized by filtration and transferred to the container by an aseptic technique. Examples of bactericidal and fungicidal agents suitable for inclusion in the drops are phenylmercuric nitrate or acetate (0.00217 c), benzalkonium chloride (0.01%) and chlorhexidine acetate (0.01%). Suitable solvents for the preparation of an oily solution include glycerol, diluted alcohol, and propylene glycol.

Lotions according to the present invention include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil. Creams, ointments, or pastes according to the present invention are semi-solid formulations of the active ingredient for external application. They may be made by mixing the active ingredient in finely divided or powdered form, alone or in solution or suspension in an aqueous or non-aqueous fluid, with the aid of suitable machinery, with a greasy or non-greasy basis. The basis may comprise hydrocarbons such as hard, soft or liquid paraffin, glycerol, beeswax, a metallic soap; a mucilage; an oil of natural origin such as almond, corn, arachis, castor or olive oil; wool fat or its derivatives, or a fatty acid such as stearic or oleic acid together with an alcohol such as propylene glycol or macrogols. The formulation may incorporate any suitable surface-active agent such as an anionic, cationic, or non-ionic surface-active agent such as sorbitan esters or polyoxyethylene derivatives thereof. Suspending agents such as natural gums, cellulose derivatives or inorganic materials such as silicaceous silicas, and other ingredients such as lanolin may also be included. Other adjuvants and modes of administration are well and widely known in the pharmaceutical art. Although this invention has been described with respect to specific embodiments, the details of these embodiments are not to be construed as limitations.

Another aspect of the present invention is chemical intermediates useful in the synthesis of the compounds of Formula I and II.

Another aspect of the present invention is methods of syntheses of the compounds of Formula I and II.

General Synthetic Procedures

The starting materials used herein are commercially available or are prepared by routine methods well known to those of ordinary skill in the art and can be found in standard reference books, such as the COMPENDIUM OF ORGANIC SYNTHETIC METHODS, Vol. I–VI (published by Wiley-Interscience).

The compounds of the invention can be synthesized according to the following procedures of Schemes I–X, wherein the R1–R16 substituents, linker A, are as defined for Formula I and II, above, except where further noted.

SCHEME I

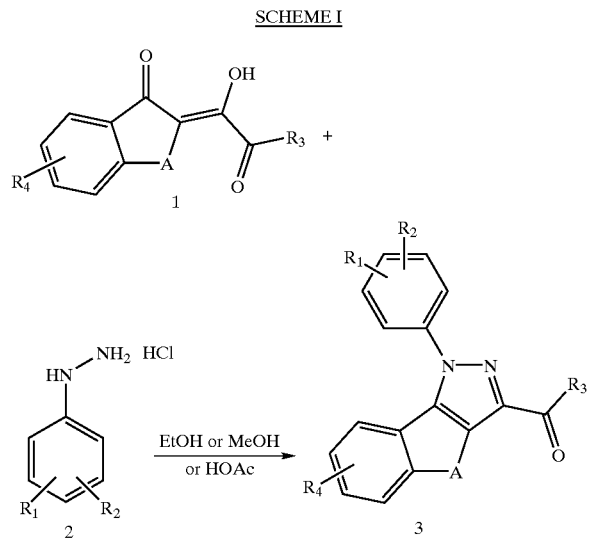

Synthetic Scheme I illustrates the procedure used to prepare the antiinflammatory pyrazoles of the present invention. 1,3-Dicarbonyl compounds such as 1, or the shown enol form which is in equilibrium with the 1,3-diketone, are allowed to react with a substituted hydrazine hydrochloride 2 in warm methanol or ethanol or acetic acid to provide the pyrazoles 3 via a condensation reaction. When A=—CH$_2$CH$_2$—, the central ring may be aromatized to provide A=—CH=CH—, by using an oxidant such as DDQ, Pd or Pt on carbon with cyclooctadiene or other H$_2$ acceptor, or sulfur in an appropriate solvent.

SCHEME II

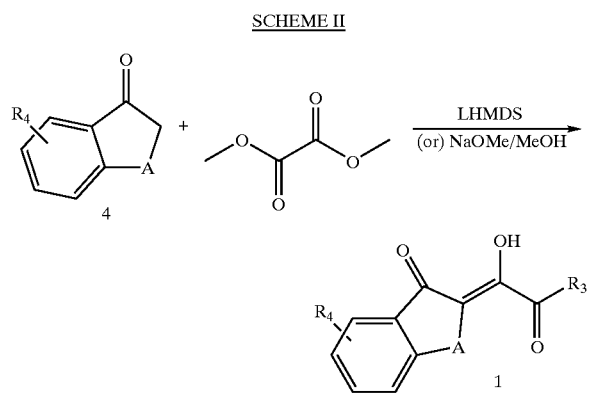

Synthetic Scheme II illustrates the procedure for the preparation of substituted diketones 1. An appropriately substituted ketone 4, including, but not limited to; 1-indanones, 1-tetralones, and 1-benzosuberones, is first treated with base, such as sodium methoxide, lithium bistrimethylsilylamide or lithium diisopropylamide (LDA), followed by condensation with a suitable acylating agent, such as, dimethyl or diethyl oxalate, in an appropriate solvent, such as methanol, diethyl ether or tetrahydrofuran, to provide 1,3-dicarbonyl compounds 1 which are suitable for conversion into antiinflammatory pyrazoles as illustrated in Scheme I. Alternatively, the dicarbonyl compounds 1 can be directly prepared from commercially available cyclic ketones 4.

SCHEME III

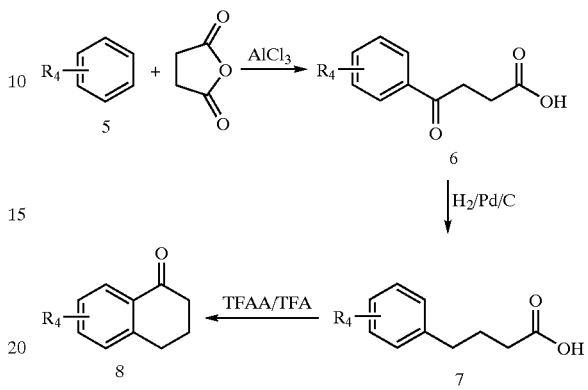

Synthetic Scheme III illustrates a three-step procedure used for the preparation of substituted 1-tetralones. In step one, an appropriate substituted benzene 5 is condensed with succinic anhydride and a catalyst such as aluminum chloride into the corresponding 4-phenyl-4-ketobutanoic acid derivatives 6. In step two, the keto group of the 4-phenyl-4-ketobutanoic acids 6 is reduced using catalytic hydrogenation or Wolff-Kishner type reductions, thus providing 4-phenylbutanoic acids 7. In addition, ketone reductions can be carried out using metal amalgams. In step three, the 4-phenylbutanoic acids are treated with a mixture of trifluoroacetic anhydride, and trifluoroacetic acid to effect intramolecular Friedel-Crafts acylation affording selected tetralones 8. Alternatively, the Friedel-Crafts acylation can be affected with other strong acids such as polyphosphoric acid, sulfuric acid or aluminum chloride.

SCHEME IV

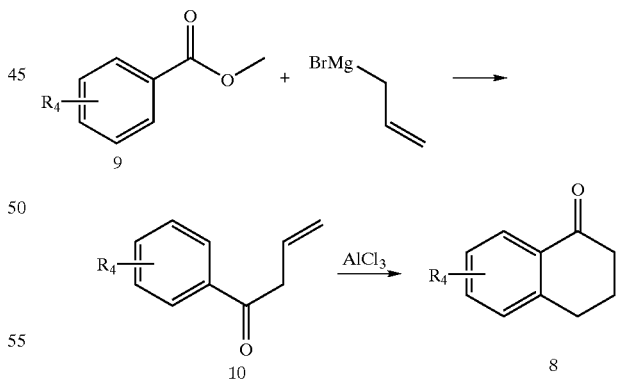

Synthetic Scheme IV describes an alternate synthetic route to 1-tetralones 8. In step one, addition of allylmagnesium bromide in a suitable solvent such as, THF or diethyl ether, to an appropriately substituted benzoate 9 affords the 1-phenylbut-3-ene-1-ones 10. In step two, the 1-phenylbut-3-ene-1-ones 10 can be cyclized under Friedel-Crafts alkylation conditions, provided R4 is a ring activating substituent, using catalysts such as aluminum chloride to produce 1-tetralones 8.

SCHEME V

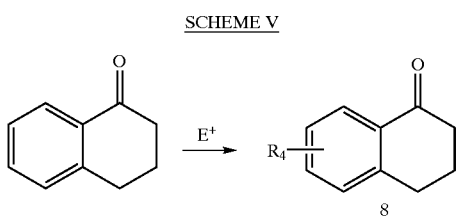

Scheme V describes the direct modification of 1-tetralone to substituted tetralones. Commercially available 1-tetralone may be treated with a variety of electrophilic reagents such as bromine, ammonium nitrite or vinylsilanes, represented by $E^+$, with or without a catalyst to generate directly a substituted tetralone 8, containing bromo, nitro or vinyl groups. Such tetralones 8 can be further embellished to provide the desired substitution patterns. Mixtures may be readily separated using chromatographic techniques.

SCHEME VI

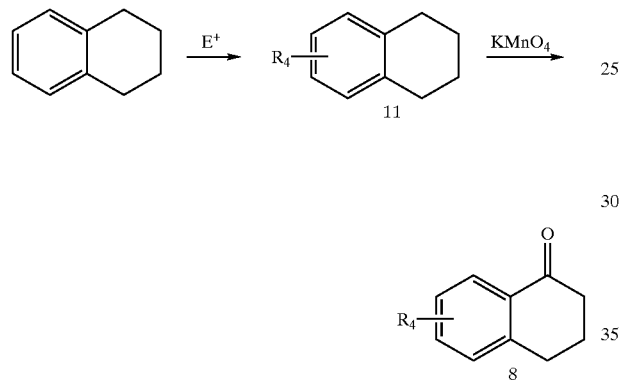

An alternate to Scheme V is Scheme VI wherein an appropriately substituted decaline is subjected to electrophilic addition to generate substituted decalins 11. Substituted decalins may also be prepared by Friedel-Crafts alkylation of substituted benzenes. Substituted decalins 11 can then be oxidized to the tetralones 8 using oxidants such as $KMnO_4$ or $SeO_2$.

SCHEME VII

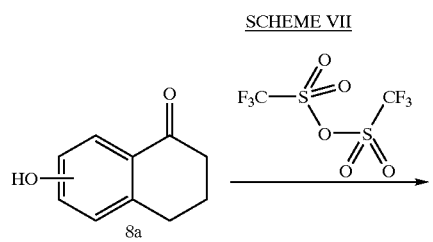

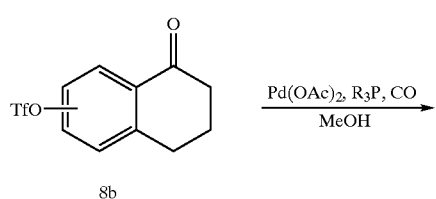

Scheme VII describes the modification of existing tetralones into analogs containing differing functional groups that can also be further modified. By example, hydroxy tetralone (8a where $R_4$=OH) can be converted to the triflate 8b by treatment with trifluoromethane sulfonic anhydride. Triflate 8b can the be subjected to $Pd(OAc)_2$ an appropriate phosphine and CO in the presence of methanol to generate tetralone 12 containing a carboxy methyl group. Triflates can be used in a variety of palladium coupling reactions to introduce additional functional groups.

SCHEME VIII

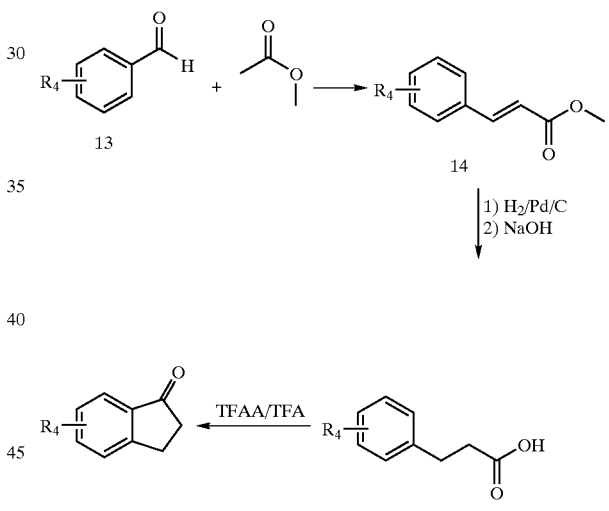

Synthetic Scheme VIII illustrates a three step procedure used for the preparation of substituted 1-indanones 16. In step one, an appropriate substituted benzaldehyde 13 is condensed with methyl acetate and a catalyst such as triethylamine into the corresponding methyl cinnamate derivatives 14. Additionally, commercially available cinnamates may be used in the following steps. In step two the olefin group of the cinnamate 14 is reduced using catalytic hydrogenation and the ester hydrolyzed with base, such as NaOH, thus providing 3-phenylpropanoic acids 15. In step three, the 3-phenylpropanoic acids are treated with a mixture of trifluoroacetic anhydride and trifluoroacetic acid to effect intramolecular Friedel-Crafts acylation affording selected 1-indanones 16. Alternatively, the Friedel-Crafts acylation can be effected with other strong acids such as sulfuric acid or aluminum chloride.

SCHEME IX

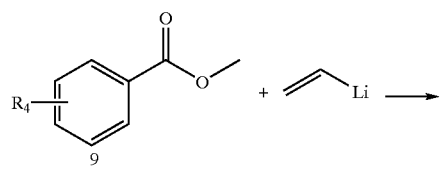

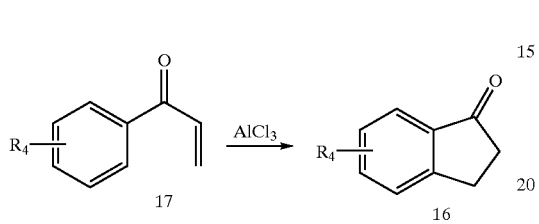

Synthetic Scheme IX illustrates a two-step route for the preparation of substituted 1-indanones 16. Commercially available methyl benzoates 9, or other alkyl esters, may be treated with a vinyl lithium reagent to afford phenylvinyl ketones 17. Alternatively, dimethylamides or N-methyl-O-methylhydroxamides may be used in place of the esters. Also, other vinyl metals, such as; vinylmagnesium bromide may be used in place of the vinyl lithium reagent. The resulting phenylvinyl ketones may be cyclized using Friedel-Crafts alkylating catalysts, such as aluminum chloride.

SCHEME X

Synthetic Scheme X illustrates a three step procedure used for the preparation of substituted 1-benzosuberones 20. In step one, an appropriate substituted benzene 5 is condensed with glutaric anhydride and a catalyst such as aluminum chloride into the corresponding 5-phenyl-5-ketopentanoic acid derivatives 18. In step two, the keto group of the 5-phenyl-5-ketopentanoic acids 18 is reduced using catalytic hydrogenation or Wolff-Kishner type reductions, thus providing 5-phenylpentanoic acids 19. In addition, ketone reductions can also be carried out using metal amalgams. In step three, the 5-phenylpentanoic acids are treated with a mixture of trifluoroacetic anhydride, and trifluoroacetic acid to effect intramolecular Friedel-Crafts acylation affording selected benzosuberones 20. Alternatively, the Friedel-Crafts acylation can be affected with other strong acids such as polyphosphoric acid, $H_2SO_4$ or $AlCl_3$. Alternatively, 5-phenyl-5-ketopentanoic acids 18, can be prepared from glutaric acid and a phenyllithium or a phenyl Grignard reagent appropriately substituted and compatible with reaction conditions.

SCHEME XI

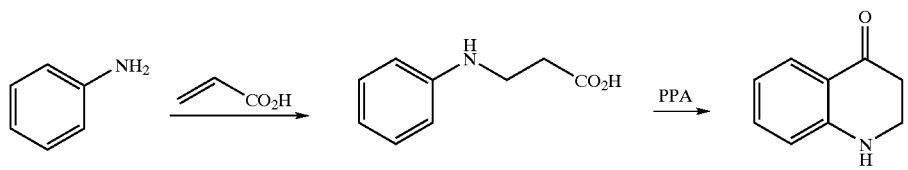

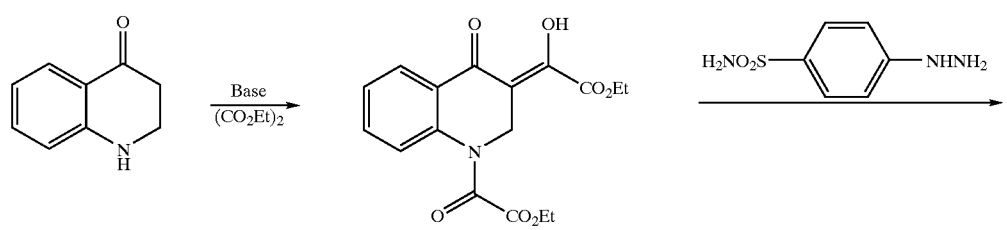

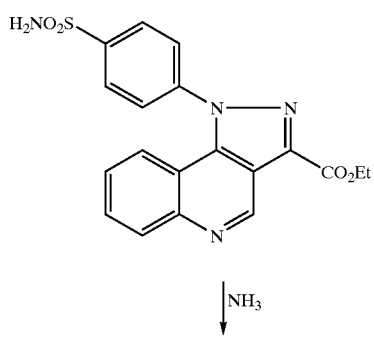
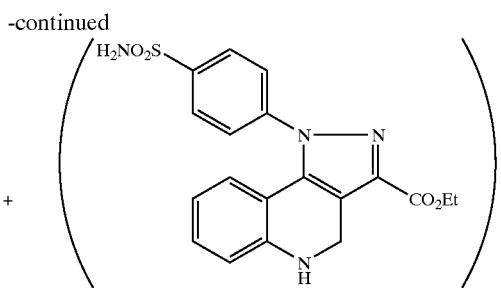

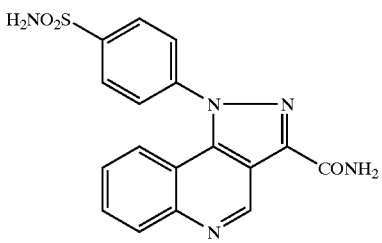

Scheme XI describes the general synthesis of pyrazolo[4,3-c]quinoline analogs of this present invention. In step 1, aniline was heated with acrylic acid in a solvent such toluene to give N-phenyl-β-aniline. In step two, the acid was treated with PPA at 100° C. to give dihydroquinolinone. In step three, the ketone was first treated with a base such as LiHMDS, followed by diethyl oxylate to afford the intermediate. This intermediate was then reacted with a substituted phenylhydrazine to form pyrazole in step four; substituents can be sulfonamide and sulfone (aromatization occurred in this reaction presumably by β-elimination). In step five; the aromatized pyrazole was converted to amide by using ammonia in ethanol.

The complete content of all publications, patents, and patent applications cited in this disclosure are herein incorporated by reference as if each individual publication, patent, or patent application were specifically and individually indicated to incorporated by reference. Although the foregoing invention has been described in some detail by way of illustration and example for the purposes of clarity of understanding, it will be readily apparent to one skilled in the art in light of the teachings of this invention that changes and modifications can be made without departing from the spirit and scope of the present invention. The following examples are provided for exemplification purposes only and are not intended to limit the scope of the invention, which has been described in broad terms above.

EXAMPLES

Example 1

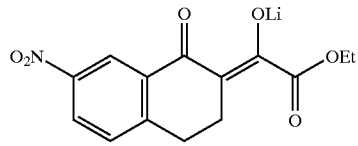

To 7-nitro-1-tetralone (4.6 g, 0.024 mol) and ethyl oxalate (3.5 mL, 0.026 mol) in ether (100 mL), was added dropwise lithium bis(trimethylsilyl)amide (1M in THF, 26 mL). The slurry was stirred overnight and filtered to give the product as an olive green solid, 6.2 g (87% yield). $^1$H NMR (DMSO-$d_6$/300 MHz) 8.45 (d, 1H); 8.05 (d of d, 1H); 7.42 (d, 1H); 4.08 (q, 2H); 2.82–2.72 (m, 2H); 2.51–2.43 (m, 2H); 1.21 (t, 3H).

Example 2

Ethyl 1-{4-[(aminothio)peroxy]phenyl}-8-nitro-4,5-dihydro-1H-benzo[g]indazole-3-carboxylate

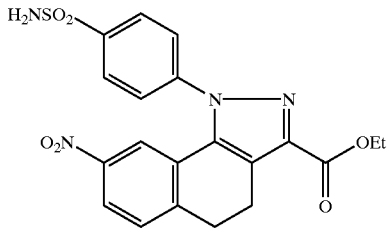

The material of Example 1 (6.2 g, 0.021 mol) and 4-sulfonamidophenylhydrazine hydrochloride (5.1 g, 0.023 mol) were stirred in methanol (100 mL) overnight. Conc. HCl (2 mL) was added to the thick slurry and the contents were heated on a steam bath for 1 hour. Contents were allowed to cool and filtered to give an off-white solid, 6.9 g. NMR and LC/MS analysis show the solid to contain two components, the desired and the hydrated pyrazole. TFA (60 mL) and TFAA (20 mL) were added to the solid and heated on a steam bath for 1 hour. Contents were concentrated in vacuo leaving the product as a solid, 6.4 g (69% yield). FABHRMS m/z 443.1020 (M+H, $C_{20}H_{19}N_4O_6S$ requires 443.1025). $^1$H NMR (DMSO-$d_6$/300 MHz) 8.10 (d of d, 1H); 8.03 (d, 2H); 7.82 (d, 2H); 7.70 (d, 1H); 7.62 (s, 1H); 7.50 (d, 1H); 4.33 (q, 2H); 3.20–2.95 (m, 4H); 1.33 (t, 3H). Anal. Calcd for $C_{20}H_{18}N_4O_6S$: C, 54.29; H, 4.10; N, 12.66. Found: C, 54.49; H, 4.00; N, 12.52.

Example 3

1-{4-[(aminothio)peroxy]phenyl}-8-nitro-4,5-dihydro-1H-benzo[g]indazole-3-carboxamide

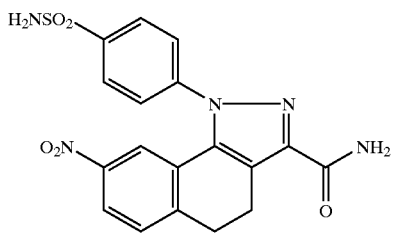

The material of Example 2 (718 mg, 0.0016 mol), conc. ammonium hydroxide (30 mL), and methanol (15 mL) were stirred in a stoppered flask for 72 hours. Contents were filtered to give a light amber solid (606 mg). The solid was recrystallized from acetonitrile to give the product as a light amber solid, 450 mg (68% yield). FABHRMS m/z 414.0902 (M+H, $C_{18}H_{16}N_5O_5S$ requires 414.0872). $^1$H NMR (DMSO-$d_6$/300 MHz) 8.15–7.95 (m, 3H); 7.83 (d, 2H); 7.80–7.40 (m, 6H); 3.20–2.95 (m, 4H). Anal. Calcd for $C_{18}H_{15}N_5O_5S$: C, 52.30; H, 3.66; N, 16.94. Found: C, 52.04; H, 3.64; N, 16.61.

Example 4a

Ethyl 8-amino-1-{4-[(aminothio)peroxy]phenyl}-4,5-dihydro-1H-benzo[g]indazole-3-carboxylate

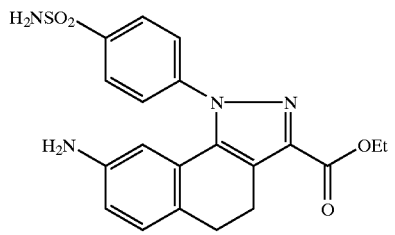

The product of Example 2 (2.0 g) and 10% Pd/C (350 mg) in DMF (20 mL) were shaken at 55 psi hydrogen for 3 hours. The catalyst was removed by filtration and the filtrate was concentrated under vacuum to yield a yellow wax. The wax was triturated with methanol and the resulting amber solid was collected by filtration to afford the title compound (1.6 g).

Example 4b 8-amino-1-{4-[(aminothio)peroxy]phenyl}-4,5-dihydro-1H-benzo[g]indazole-3-carboxamide

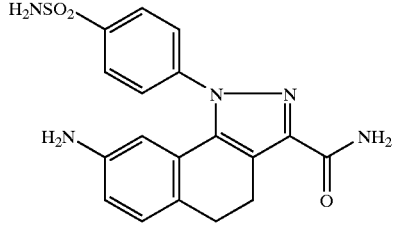

The product of Example 4a (968 mg), conc. ammonium hydroxide (10 mL), and methanol (5 mL) were heated at 95° C. in a sealed pressure bottle for 16 h. The mixture was allowed to cool and let stand for 3 h. The resulting amber solid was collected by filtration to yield the title compound (630 mg).

FABHRMS m/z 384.1136 (M+H, $C_{18}H_{18}N_5O_3S$ requires 384.1130). $^1$H NMR (DMSO-$d_6$/300 MHz) 7.95 (d, 2H); 7.75 (d, 2H); 7.53 (br s, 1H); 7.43 (br s, 1H); 7.32 (br s, 1H); 7.01 (d, 1H); 6.44 (d of d, 1H); 6.03 (s, 1H); 4.81 (s, 2H); 2.93–2.65 (m, 4H). Anal. Calcd for $C_{18}H_{17}N_5O_3S$: C, 56.38; H, 4.47; N, 18.27. Found: C, 56.31; H, 4.42; N, 18.31.

Example 4c 8-amino-1-{4-[(aminothio)peroxy]phenyl}-1H-benzo[g]indazole-3-carboxamide

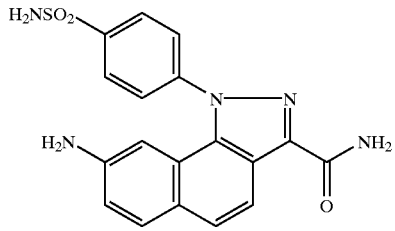

The product of Example 4b (1 g) and 5% Pd/C (300 mg) suspended in cumene (50 mL) and NMP (5 mL) was heated at reflux for 16 h. The mixture was then filtered and concentrated. The residue was diluted with methanol (10 mL) and added to water, after 1 h the resulting precipitate was collected by filtration and dried to yield the title compound (0.9 g).

Example 5

8-(acetylamino)-1-{4-[(aminothio)peroxy]phenyl}-4,5-dihydro-1H-benzo[g]indazole-3-carboxamide

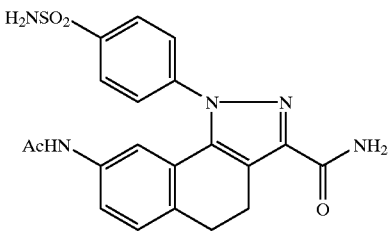

To the material of Example 4b (1.0 g, 0.0026 mol) in DMF (15 mL) was added dropwise a mixture of acetic anhydride (0.283 mL, 0.003 mol) and pyridine (0.243 mL, 0.003 mol) in DMF (5 mL). Contents were stirred overnight, diluted with water (75 mL), and filtered to give the desired as a white solid, 1.0 g (90% yield). FABHRMS m/z 426.1235 (M+H, $C_{20}H_{20}N_5O_4S$ requires 426.1236). $^1$H NMR (DMSO-$d_6$/300 MHz) 9.80 (s, 1H); 8.00 (d, 2H); 7.75 (d, 2H); 7.60 (s, 1H); 7.48 (s, 2H); 7.39 (s, 1H); 7.30 (d, 1H); 7.15 (s, 1H); 2.90 (s, 4H); 1.92 (s, 3H). Anal. Calcd for $C_{20}H_{19}N_5O_4S$ (1H$_2$O): C, 54.17; H, 4.77; N, 15.79. Found: C, 54.20; H, 4.97; N, 15.77.

Example 6

1-{4-[(aminothio)peroxy]phenyl}-8-{[(methylthio)peroxy]amino}-4,5-dihydro-1H-benzo[g]indazole-3-carboxamide

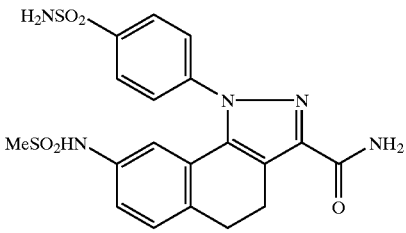

To the material of Example 4 (1.2 g, 0.003 mol) and triethylamine (0.278 mL, 0.0035 mol) in DMF (10 mL) at 0° C., was added dropwise methanesulfonyl chloride (0.278 mL, 0.0035 mol) in CH$_2$Cl$_2$ (2 mL). Contents were stirred overnight, slowly coming to room temperature. Contents were diluted with water (50 mL) and filtered to give the product as an off-white solid, 524 mg (37% yield). FAB-HRMS m/z 462.0917 (M+H, $C_{19}H_{20}N_5O_5S_2$ requires 462.0906). $^1$H NMR (DMSO-$d_6$/300 MHz) 9.60 (s, 1H); 7.98 (d, 2H); 7.80 (d, 2H); 7.60 (s, 1H); 7.50 (s, 2H); 7.40 (s, 1H); 7.37 (d, 1H); 7.02 (s, 1H); 6.75 (s, 1H); 2.93 (s, 4H); 2.75 (s, 3H). Anal. Calcd for $C_{19}H_{19}N_5O_5S_2$: C, 49.45; H. 4.15; N. 15.17. Found: C, 49.19; H, 3.77; N, 15.53.

Examples 7–34

Synthesis of the Sulfonamide/Amide/Urea Library

SCHEME XII

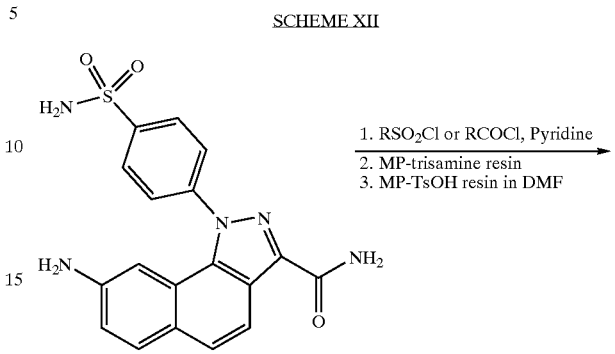

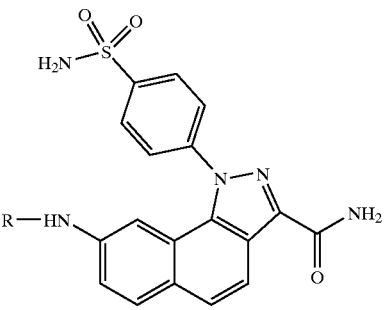

The sulfonamides, amides, and urea were synthesized in a library format by using a Bohdan reaction block. The starting materials are 8-amino-1-{4-[(aminothio)peroxy]phenyl}-4,5-dihydro-1H-benzo[g]indazole-3-carboxamide (Example 4) and appropriate sulfonyl chlorides, acyl chlorides and isocyanates. Twenty-eight reactions were done in this library.

The general procedure is as follows: 48 mg of 8-amino-1-{4-[(aminothio)peroxy]phenyl}-1H-benzo[g]indazole-3-carboxamide in 1 mL pyridine was placed in each reaction vessel, then 1.2 eq. of a sulfonyl chloride was added, and the mixture was shaken overnight. Then 3 mL methylene chloride and 300 mg of resin PS-trisamine were added, and then shaken over night. After filtration and washing with 2 mL methanol twice, the filtrates were combined and solvents evaporated. The residue was dissolved in 2 mL dimethylformamide, and MS-TsOH resin (450 mg) was added and shaken for 48 hours. After filtration and washing with 2 mL DMF, the combined filtrate was analyzed by LC-MS and LC. Then the filtrate was evaporated on a SpeedVac and the residue were suspended in 2 mL of H$_2$O/tBuOH, and lyophilized for 2 days. All compounds were obtained in solid form, and the majority of the compounds have about 90% purity. Table 1 shows the compound identification, structure, IKK heterodimer assay values (expressed as IC50), and weight (determined by Mass Spectroscopy) for the compounds from the sulfonamide library.

Table 1 shows the compound identification, compound, IKK heterodimer assay values expressed as IC$_{50}$, formula weight, and mass spectroscopy characterization for the compounds from the library.

TABLE 1

| COMPOUND | STRUCTURE | EXAMPLE | Formula HetD Weight | Mass Spec |
|---|---|---|---|---|
| 8-amino-1-{4-[(aminothio)peroxy]phenyl}-1H-benzo[g]indazole-3-carboxamide | 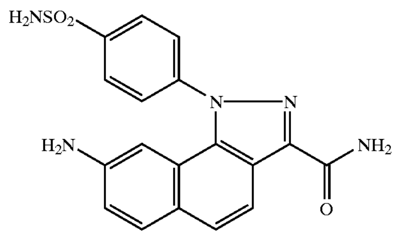 | Example 4c | ≦1 μM  381.41 | 382 |
| 8-amino-1-{4-[(diallylamino)sulfonyl]phenyl}-1H-benzo[g]indazole-3-carboxamide | 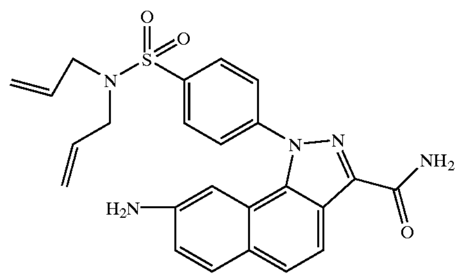 | Example 7 | ≦1 μM  461.54 | 462 |
| 1-[4-(aminosulfonyl)phenyl]-8-[(3-methoxybenzoyl)amino]-1H-benzo[g]indazole-3-carboxamide | 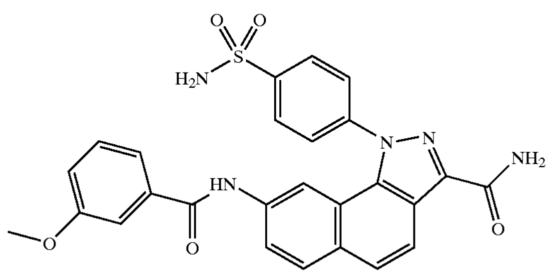 | Example 8 | ≦1 μM  515.55 | 516 |
| 1-[4-(aminosulfonyl)phenyl]-8-[(3-chlorobenzoyl)amino]-1H-benzo[g]indazole-3-carboxamide | 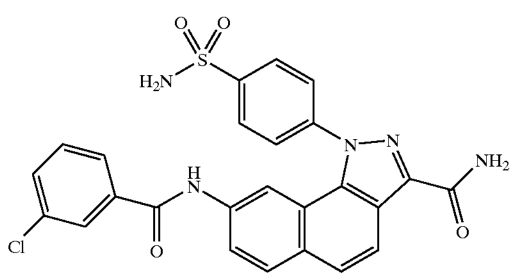 | Example 9 | ≦1 μM  519.97 | 520 |
| 1-[4-(aminosulfonyl)phenyl]-8-{[3-(trifluoromethyl)benzoyl]amino}-1H-benzo[g]indazole-3-carboxamide | 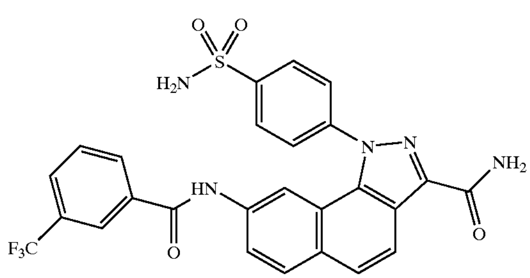 | Example 10 | 1 ≦ 10 μM  553.52 | 554 |

TABLE 1-continued

| COMPOUND | STRUCTURE | EXAMPLE | HetD | Formula Weight | Mass Spec |
|---|---|---|---|---|---|
| 1-[4-(aminosulfonyl)phenyl]-8-[(3-methylbenzoyl)amino]-1H-benzo[g]indazole-3-carboxamide | 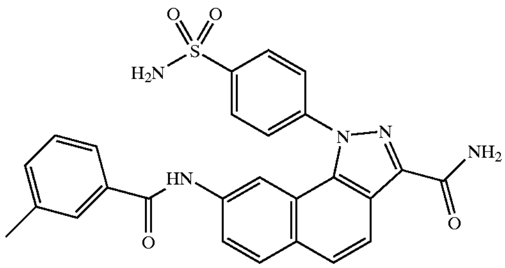 | Example 11 | ≦1 μM | 499.55 | 500 |
| 1-[4-(aminosulfonyl)phenyl]-8-[(3-bromobenzoyl)amino]-1H-benzo[g]indazole-3-carboxamide | 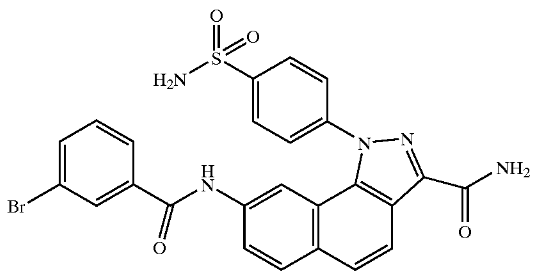 | Example 12 | ≦1 μM | 564.42 | 565 |
| 1-[4-(aminosulfonyl)phenyl]-8-[(pyridin-3-ylcarbonyl)amino]-1H-benzo[g]indazole-3-carboxamide | 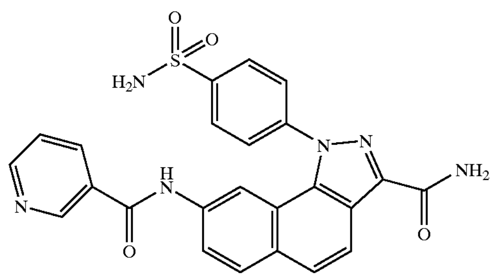 | Example 13 | ≦1 μM | 486.51 | 487 |
| 1-[4-(aminosulfonyl)phenyl]-8-[(2-chlorobenzoyl)amino]-1H-benzo[g]indazole-3-carboxamide | 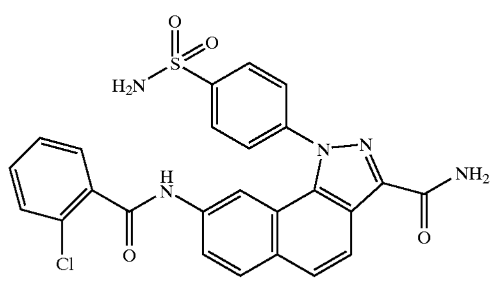 | Example 14 | ≦1 μM | 519.97 | 520 |
| 1-[4-(aminosulfonyl)phenyl]-8-{[(3-bromophenyl)sulfonyl]amino}-1H-benzo[g]indazole-3-carboxamide | 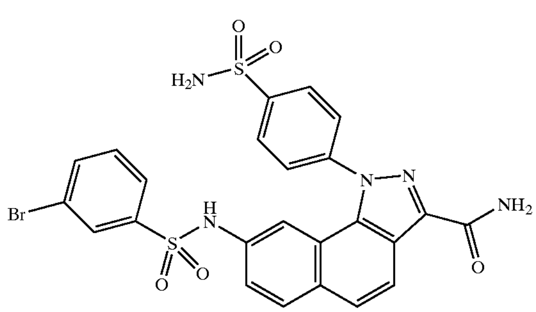 | Example 15 | 1 ≦ 10 μM | 600.47 | 601 |

TABLE 1-continued

| COMPOUND | STRUCTURE | EXAMPLE | HetD | Formula Weight | Mass Spec |
|---|---|---|---|---|---|
| 1-[4-(aminosulfonyl)phenyl]-8-{[(3-chlorophenyl)sulfonyl]amino}-1H-benzo[g]indazole-3-carboxamide | 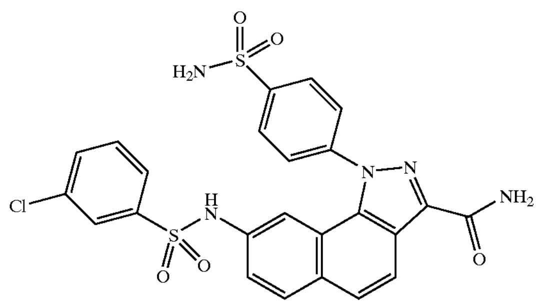 | Example 16 | 1 ≦ 10 μM | 556.02 | 557 |
| 1-[4-(aminosulfonyl)phenyl]-8-[(3-cyanobenzoyl)amino]-1H-benzo[g]indazole-3-carboxamide | 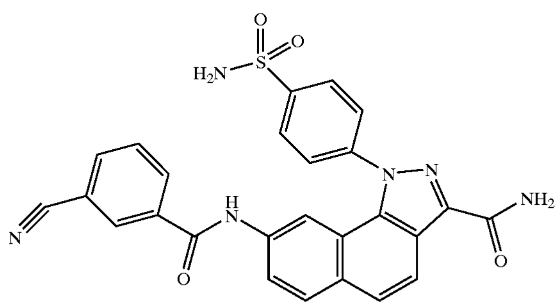 | Example 17 | ≦1 μM | 510.53 | 511 |
| 1-[4-(aminosulfonyl)phenyl]-8-{[(3-methylphenyl)sulfonyl]amino}-1H-benzo[g]indazole-3-carboxamide | 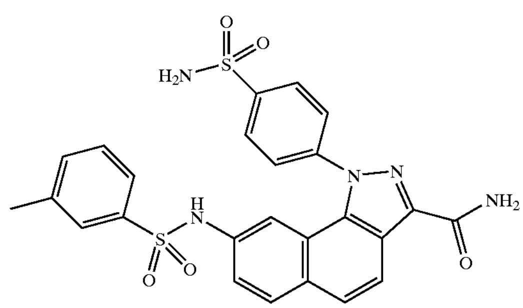 | Example 18 | 10 ≦ 100 μM | 535.6 | 536 |
| 1-[4-(aminosulfonyl)phenyl]-8-({[3-(trifluoromethyl)phenyl]sulfonyl}amino)-1H-benzo[g]indazole-3-carboxamide | 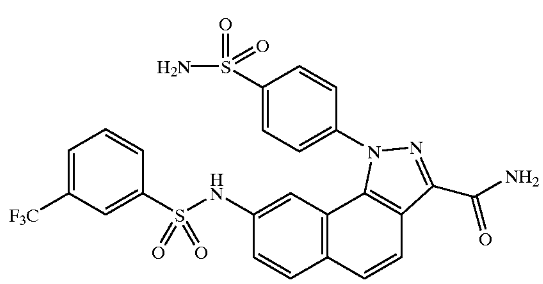 | Example 19 | 10 ≦ 100 μM | 589.57 | 590 |
| 8-(acetylamino)-1-[4-(aminosulfonyl)phenyl]-1H-benzo[g]indazole-3-carboxamide | 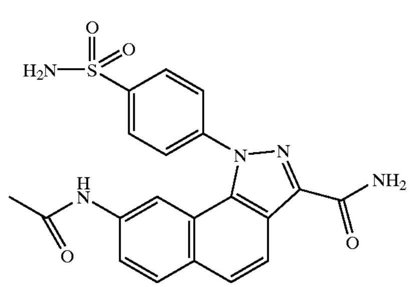 | Example 20 | ≦1 μM | 423.45 | 424 |

TABLE 1-continued

| COMPOUND | STRUCTURE | EXAMPLE | HetD | Formula Weight | Mass Spec |
|---|---|---|---|---|---|
| 1-[4-(aminosulfonyl)phenyl]-8-[(methylsulfonyl)amino]-1H-benzo[g]indazole-3-carboxamide | 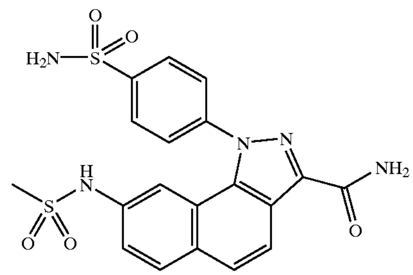 | Example 21 | ≦1 μM | 459.51 | 460 |
| 1-[4-(aminosulfonyl)phenyl]-8-{[(3,4-dichlorophenyl)sulfonyl]amino}-1H-benzo[g]indazole-3-carboxamide | 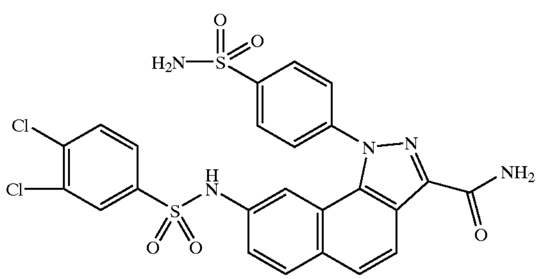 | Example 22 | 1 ≦ 10 μM | 590.47 | 591 |
| 1-[4-(aminosulfonyl)phenyl]-8-{[(2,4,5-trichlorophenyl)sulfonyl]amino}-1H-benzo[g]indazole-3-carboxamide | 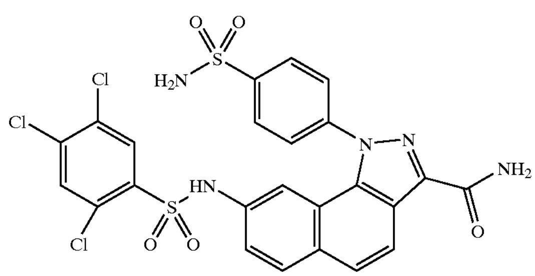 | Example 23 | 1 ≦ 10 μM | 624.91 | 625 |
| 1-[4-(aminosulfonyl)phenyl]-8-({[3,5-bis(trifluoromethyl)phenyl]sulfonyl}amino)-1H-benzo[g]indazole-3-carboxamide | 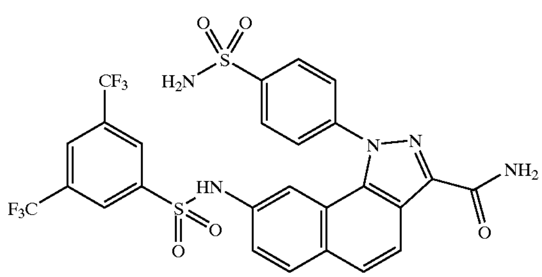 | Example 24 | 1 ≦ 10 μM | 657.57 | 658 |
| 1-[4-(aminosulfonyl)phenyl]-8-[(2-methoxybenzoyl)amino]-1H-benzo[g]indazole-3-carboxamide | 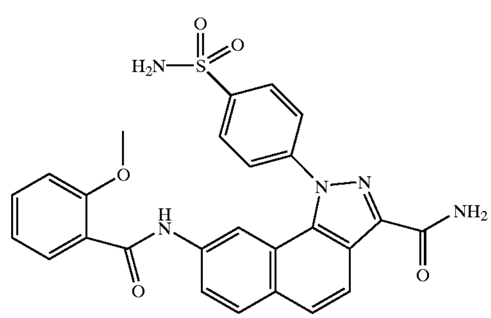 | Example 25 | 1 ≦ 10 μM | 515.55 | 516 |

TABLE 1-continued

| COMPOUND | STRUCTURE | EXAMPLE | Formula HetD Weight | Mass Spec |
|---|---|---|---|---|
| 1-[4-(aminosulfonyl)phenyl]-8-{[2-(trifluoromethyl)benzoyl]amino}-1H-benzo[g]indazole-3-carboxamide | 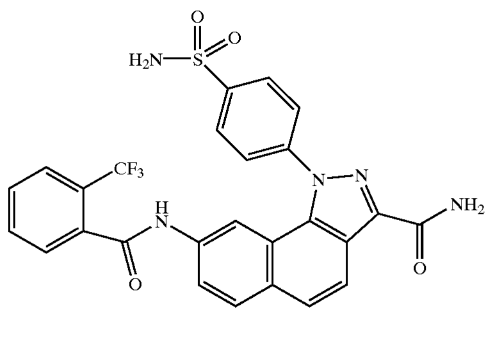 | Example 26 | ≦1 μM  553.52 | 554 |
| 1-[4-(aminosulfonyl)phenyl]-8-[(2-methylbenzoyl)amino]-1H-benzo[g]indazole-3-carboxamide | 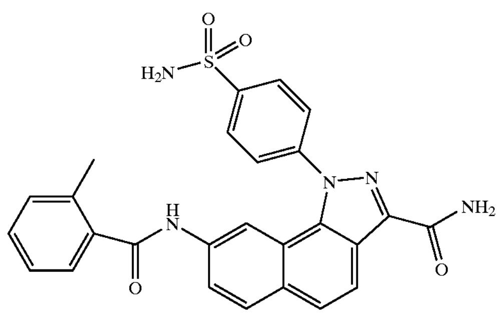 | Example 27 | ≦1 μM  499.55 | 500 |
| 1-[4-(aminosulfonyl)phenyl]-8-[(2,6-dichlorobenzoyl)amino]-1H-benzo[g]indazole-3-carboxamide | 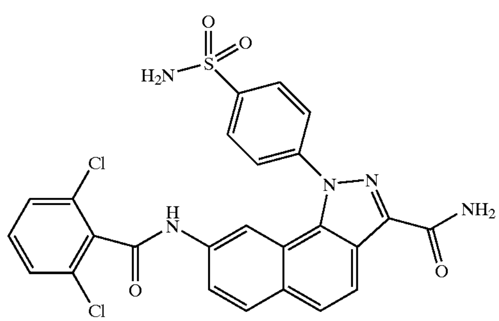 | Example 28 | ≦1 μM  554.41 | 555 |
| 1-[4-(aminosulfonyl)phenyl]-8-{[(2-(trifluoromethoxy)benzoyl]amino}-1H-benzo[g]indazole-3-carboxamide | 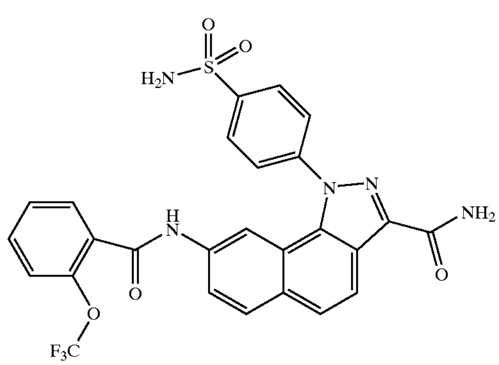 | Example 29 | ≦1 μM  569.52 | 570 |

TABLE 1-continued

| COMPOUND | STRUCTURE | EXAMPLE | HetD | Formula Weight | Mass Spec |
|---|---|---|---|---|---|
| 1-[4-(aminosulfonyl)phenyl]-8-[(2,3-dichlorobenzoyl)amino]-1H-benzo[g]indazole-3-carboxamide | 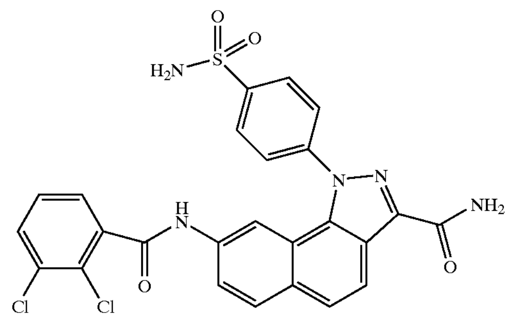 | Example 30 | ≦1 μM | 554.41 | 555 |
| 1-[4-(aminosulfonyl)phenyl]-8-[(2-fluorobenzoyl)amino]-1H-benzo[g]indazole-3-carboxamide | 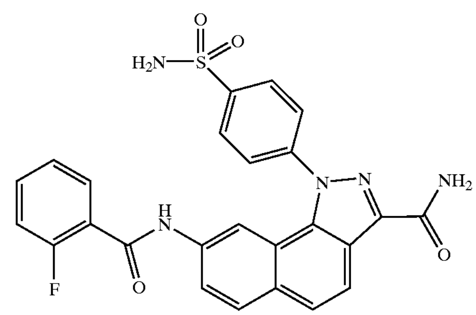 | Example 31 | ≦1 μM | 503.51 | 504 |
| 1-[4-(aminosulfonyl)phenyl]-8-{[(2-chloropyridin-3-yl)carbonyl]amino}-1H-benzo[g]indazole-3-carboxamide | 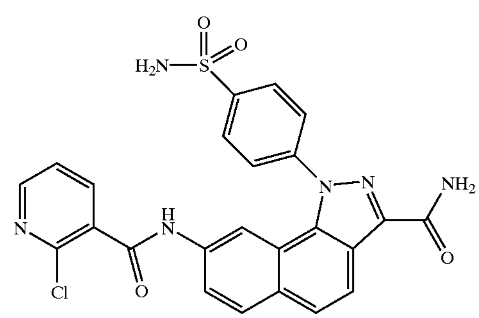 | Example 32 | ≦1 μM | 520.96 | 521 |
| 1-[4-(aminosulfonyl)phenyl]-8-{[(2-chlorophenyl)sufonyl]amino}-1H-benzo[g]indazole-3-carboxamide | 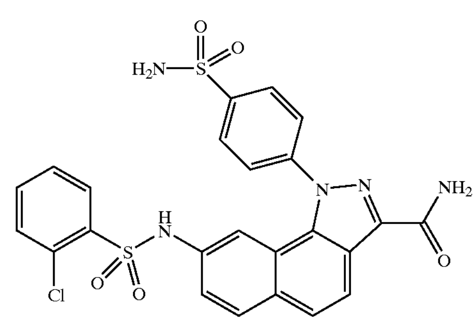 | Example 33 | 1 ≦ 10 μM | 556.02 | 557 |

TABLE 1-continued

| COMPOUND | STRUCTURE | EXAMPLE | Formula HetD Weight | Mass Spec |
|---|---|---|---|---|
| 1-[4-(aminosulfonyl)phenyl]-8-(isonicotinoylamino)-1H-benzo[g]indazole-3-carboxamide | 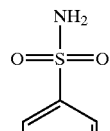 | Example 34 | ≦1 μM  486.51 | 487 |

Example 35

1-[3-(aminosulfonyl)phenyl]-8-[(2-chlorobenzoyl)amino]-1H-benzo[g]indazole-3-carboxamide

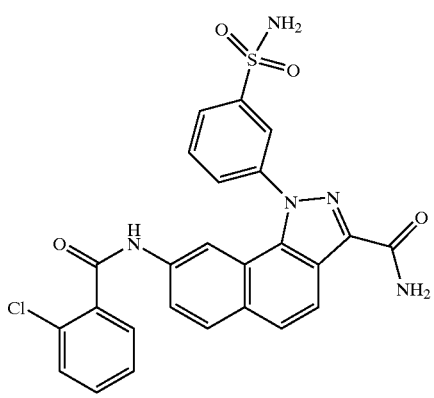

SCHEME XIII

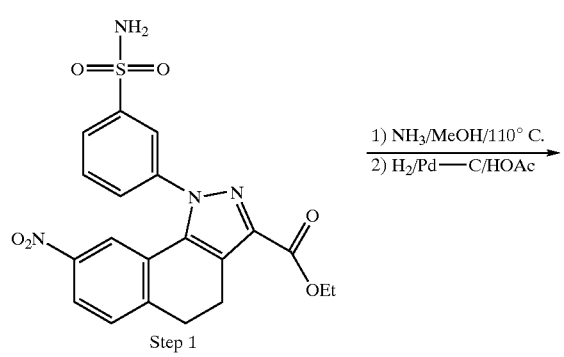

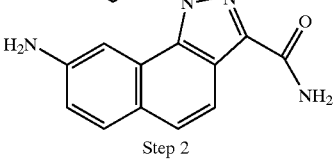

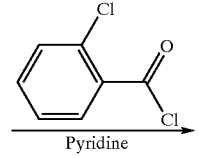

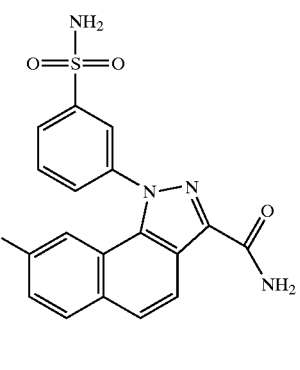

Step 3

Step 1

Ethyl 1-[3-(aminosulfonyl)phenyl]-8-nitro-4,5-dihydro-1H-benzo[g]indazole-3-carboxylate This compound was prepared using the same procedures for Ethyl 1-{4-[(aminothio)peroxy]phenyl}-8-nitro-4,5-dihydro-1H-benzo[g]indazole-3-carboxylate of Example 2, where 3-(aminosulfonamido)-phenylhydrazine was used in place of 4-(aminosulfonamido)-phenylhydrazine. Its structure was confirmed by $^1$H NMR and MS (443, M+1). $C_{20}H_{18}N_4O_6S$, Calc.: C: 54.29; H: 4.10; N: 12.66; Found, C: 54.27; H: 4.09; N: 12.55.

Step 2

8-amino-1-[3-(aminosulfonyl)phenyl]-1H-benzo[g]indazole-3-carboxamide

A sealed solution of ethyl 1-[3-(aminosulfonyl)phenyl]-8-nitro-4,5-dihydro-1H-benzo[g]indazole-3-carboxylat from step 1 (2.20 g, 4.98 mmol) in excess $NH_3$/MeOH was heated at 110° C. for 10 h. The mixture was then concentrated to 10 mL, cooled to RT and the solid product collected by filtration. The solid was dissolved in HOAc, exposed to $H_2$ (5 psi) at RT in the presence of Pd—C (5%) for 2 h. The mixture was filtered through celite pad, concentrated, taken into MeOH, filtered again through celite. The clear solution was concentrated, recrystallized in EtOH to give a grey solid (450 mg). Its structure was confirmed by $^1$H NMR and MS (382, M+1). $C_{18}H_{15}N_5O_3S.H_2O.(Et_2O)_{0.2}$, Calc.: C: 54.51, H: 4.62, N: 16.91; Found, C: 54.79, H: 4.06, N: 16.72.

Step 3

1-[3-(aminosulfonyl)phenyl]-8-[(2-chlorobenzoyl)amino]-1H-benzo[g]indazole-3-carboxamide To a stirred solution of 8-amino-1-[3-(aminosulfonyl)phenyl]-1H-benzo[g]indazole-3-carboxamide from step 2 (76.2 mg, 0.20 mmol) in pyridine (25 mL) at RT was added 2-chlorobenzoic chloride (53 mg, 0.3 mmol). After 14 h, trisamine was added and the mixture was stirred for 2 h. The mixture was filtered through a silica gel pad with EtOAc and concentrated. The resulting title product was a solid (42 mg, 40%). Its structure was confirmed by $^1$H NMR and MS (521, M+1). $C_{25}H_{18}ClN_5O_4S$, Calc.: C: 57.75, H: 3.49; N: 13.47; Found, C: 57.06, H: 3.65, N: 13.51.

Example 36

8-[(2-chlorobenzoyl)amino]-1-[4-(methylsulfonyl)phenyl]-1H-benzo[g]indazole-3-carboxamide

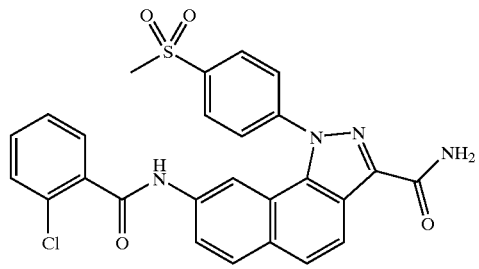

Step 1

Ethyl 1-[4-(methylsulfonyl)phenyl]-8-nitro-4,5-dihydro-1H-benzo[g]indazole-3-carboxylate

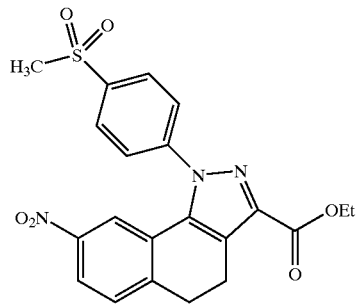

The material of Example 1 (1.88 g) was suspended in 50 ml EtOH in a round bottom flask, and then 4-metheylsulfonylphenylhydrazine (1.2 g) was added. The mixture was refluxed overnight, then the solvent evaporated, and the residue was purified by column chromatography (ethyl acetate/methylene chloride, 1/1) to yield the titled compound (0.9 g, characterized by NMR, MS and HPLC).

Step 2

1-[4-(methylsulfonyl)phenyl]-8-nitro-4,5-dihydro-1H-benzo[g]indazole-3-carboxamide

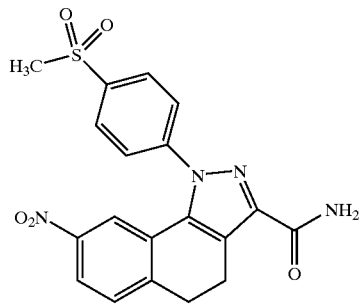

The material from step 1 (0.9 g) was subjected to aminolysis by using EtOH as solvent and ammonia at 110° C. under 400 psi for 20 hours. After the solvent was evaporated, the crude material, which was impure, was used for next step without purification or analysis.

Step 3

8-amino-1-[4-(methylsulfonyl)phenyl]-1H-benzo[g]indazole-3-carboxamide

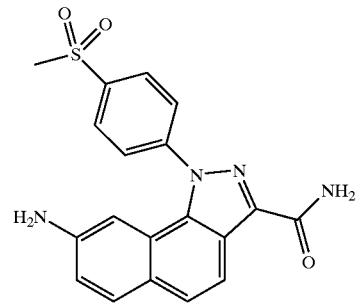

The material from the step 2 (0.9 g) was subjected to hydrogenation by using DMF-AcOH as solvent, 20% $Pd(OH)_2$/C as catalyst under 5 psi pressure for 1 hour. The solvent was evaporated, and 1 mL conc. HCl and 30 mL water were added, and the solution was filtered. The filtrate was concentrated to about 10 mL, then purified by reverse phase HPLC (5% $CH_3CN$ to 95% $CH_3CN$ in water with TFA in 30 minutes) to give the titled compound (180 mg), which was analyzed by NMR, MS, and microanalysis confirming the structure.

Step 4

8-[(2-chlorobenzoyl)amino]-1-[4-(methylsulfonyl)phenyl]-1H-benzo[g]indazole-3-carboxamide

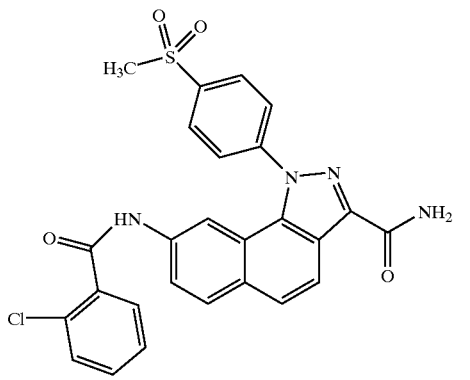

The material from step 3 (102 mg) was dissolved in 10 mL pyridine, then 2-chlorobenzoyl chloride (61 mg) in 2 mL methylene chloride was added. The mixture was stirred at room temperature for 2 hours, then MeOH (3 mL) and PS-trisamine resin (1 g) were added, and stirred overnight. After filtration and solvent evaporation, the residue obtained was suspended in tBuOH and water, and then lyophilized. The title compound (110 mg), analyzed by NMR, MS, and microanalysis, was obtained.

Examples 37–42

The compounds of Examples 37–42 shown in Table 2 were synthesized in a similar manner as described in Examples 35 and 36.

TABLE 2

| Compound No., Structure | Mol. Wt. | Compound Name(s) | IKK2 Resin IC 50 | LCMS (M + H) | Example |
|---|---|---|---|---|---|
| | 518.98 | 8-[(2-chlorobenzoyl)amino]-1-[4-(methylsulfonyl)phenyl]-1H-benzo[g]indazole-3-carboxamide | ≦1 μM | 519 | 37 |
| | 498.56 | 8-[(2-methylbenzoyl)amino]-1-[4-(methylsulfonyl)phenyl]-1H-benzo[g]indazole-3-carboxamide | ≦1 μM | 499 | 38 |
| | 552.53 | 1-[4-(methylsulfonyl)phenyl]-8-{[2-(trifluoromethyl)benzoyl]amino}-1H-benzo[g]indazole-3-carboxamide | 1 ≦ 10 μM | 553 | 39 |

TABLE 2-continued

| Compound No., Structure | Mol. Wt. | Compound Name(s) | IKK2 Resin IC 50 | LCMS (M + H) | Example |
|---|---|---|---|---|---|
| | 553.42 | 8-[(2,3-dichlorobenzoyl)amino]-1-[4-(methylsulfonyl)phenyl]-1H-benzo[g]indazole-3-carboxamide | ≦1 μM | 554 | 40 |
| | 519.97 | 8-{[(2-chloropyridin-3-yl)carbonyl]amino}-1-[4-(methylsulfonyl)phenyl]-1H-benzo[g]indazole-3-carboxamide | ≦1 μM | 520 | 41 |
| | 502.52 | 8-[(2-fluorobenzoyl)amino]-1-[4-(methylsulfonyl)phenyl]-1H-benzo[g]indazole-3-carboxamide | 1 ≦ 10 μM | 503 | 42 |

Example 43

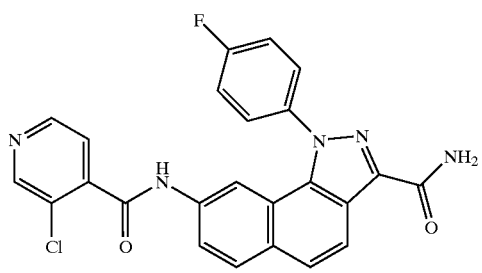

Step 1

Ethyl 1-(4-fluorophenyl)-8-nitro-4,5-dihydro-1H-benzo[g]indazole-3-carboxylate

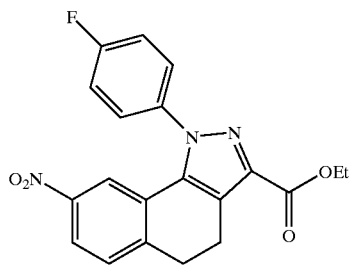

This compound was synthesized in a similar manner as described in Example 36 step 1 using 4-fluorophenylhydrazine and the material of Example 1.

Step 2

Ethyl 8-amino-1-(4-fluorophenyl)-4,5-dihydro-1H-benzo[g]indazole-3-carboxylate

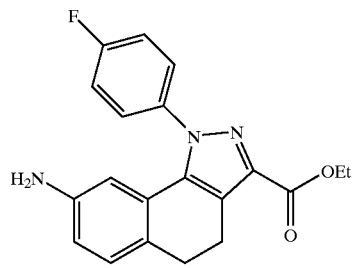

This compound was synthesized in a similar manner as described in Example 4a.

Step 3

8-amino-1-(4-fluorophenyl)-4,5-dihydro-1H-benzo[g]indazole-3-carboxamide

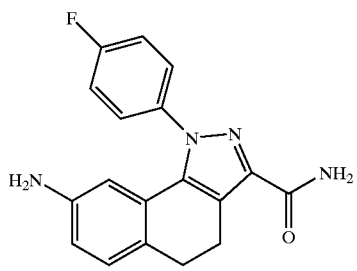

This compound was synthesized in a similar manner as described in Example 4b.

Step 4

8-amino-1-(4-fluorophenyl)-1H-benzo[g]indazole-3-carboxamide

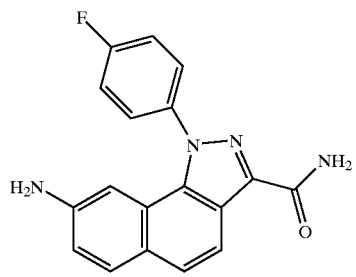

The product of step 3 (2 g) was stirred in cumene (150 mls) and warmed to 75 degrees to effect solution. Pd/C (5%; 1 g) was added and the contents were refluxed overnight under Ar. The reaction mixture was filtered hot thru a fritted filter and the Pd/C was washed with hot ethyl acetate. The filtrate was evaporated and the residue was triturated with toluene, filtered, and air dried to give 1.9 g (90%) of titled material. LCMS and NMR are consistent for the titled material.

Step 5

8-[(3-chloroisonicotinoyl)amino]-1-(4-fluorophenyl)-1H-benzo[g]indazole-3-carboxamide

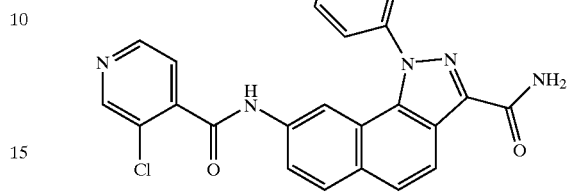

3-chloro-4-pyridylcarboxylic acid (125 mg; 0.00078 moles) was dissolved in DMF (6 mls) and diisopropylethylamine (110 mg; 1.2 equivalents) and HATU (330 mg; 1.1 equivalents) were added and the contents were stirred at room temperature under $N_2$ for 30 minutes. The material of step 4 of Example 43 (250 mg; 0.00078 moles) was added and the mixture was stirred overnight at room temperature. Contents of the reaction mixture were poured into water (30 mls) with stirring, the precipitate was filtered, and air dried. The crude product was recrystallized from EtOH/water to give the purified product (300 mg; 84%). LCMS and NMR were consistent for the titled material. $C_{24}H_{15}FClN_5O_2$. MW=459.87. Calc:C, 62.68; H, 3.29; N, 15.23. Found: C, 62.29; H, 3.51; N, 15.01.

Synthesis of Examples 44 and 45

SCHEME XIV

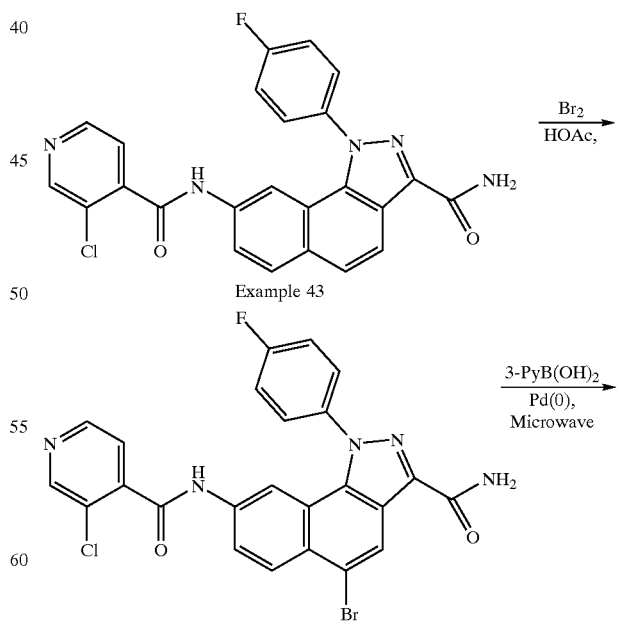

Example 44

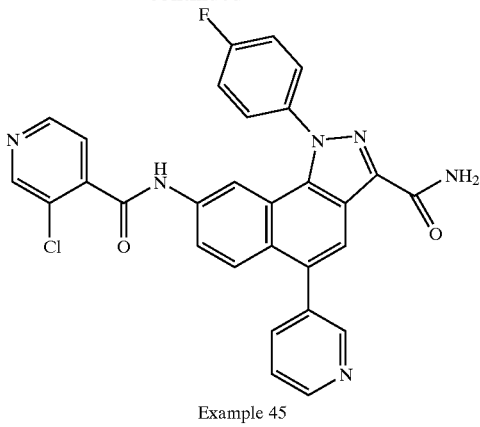

Example 45

Example 44

The title compound of Example 44 (460 mg) is suspended in 5 ml of DMF, then bromine (340 mg) in 15 ml of acetic acid was added in two portions, and the reaction mixture was stirred at room temperature for 15 minutes. After evaporation of the solvent, the residue was suspended in aq. NaHCO3, then filtered and washed with water, ether, acetonitrile. After drying under vacuum, 0.37 g of desired compound was obtained and characterized by HPLC, LC-MS, 1HMR. NOE study confirmed the substitution position.

Example 45

The title compound of Example 44 (0.27 g) is suspended in DME (5 ml) and water (1 ml). Under N2, Pd(PPh3)$_4$ (50 mg), Na2CO3 (426 mg) and 3-pyridylboronic acid (130 mg) are added. The reaction mixture was placed in CEM Discover microwave reactor at 120C for 60 minutes with 150W power. After the reaction was completed, and solvent evaporated, the residue was dissolved in 30 ml MeOH and 5 drops of conc. HCl, and purified by reversed phase HPLC(20% CH3CH to 80% CH3CN in 30 minutes). 80 mg of desired compound was obtained and characterized by LC-MS, 1HNMR, CHN analysis, and HPLC purity analysis.

Examples 46–53

The compounds of Examples 46–53 shown in Table 3 were synthesized as in Examples 44 and 45 using the approriate aryl, substituted aryl, heteroaryl, substituted heteroaryl, substituted arylalkyl, substituted heteroarylalkyl, or cycloalkyl.

The bioactivity in the IKK2 Resin assay for the compounds of Examples 43–53 is shown in Table 3.

TABLE 3

| Compound No., Structure | Mol. Wt. | Compound Name(s) | IKK2 Resin IC 50 | LCMS (M + H) | Example |
|---|---|---|---|---|---|
|  | 459.87 | 8-[(3-chloroisonicotinoyl(amino]-1-(4-fluorophenyl)-1H-benzo[g]indazole-3-carboxamide | ≦1 μM | 460 | 43 |
|  | 538.77 | 5-bromo-8-[(3-chloroisonicotinoyl(amino]-1-(4-fluorophenyl)-1H-benzo[g]indazole-3-carboxamide | ≦1 μM | 539 | 44 |
|  | 609.88 | 8-[(3-chloroisonicotinoyl(amino]-1-(4-fluorophenyl)-5-pyridin-3-yl-1H-benzo[g]indazole-3-carboxamide dihydrochloride | 1 ≦ 10 μM | 610 | 45 |

TABLE 3-continued

| Compound No., Structure | Mol. Wt. | Compound Name(s) | IKK2 Resin IC 50 | LCMS (M + H) | Example |
|---|---|---|---|---|---|
| 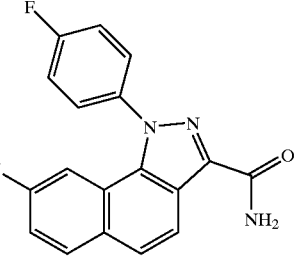 | 320.33 | 8-amino-1-(4-fluorophenyl)-1H-benzo[g]indazole-3-carboxamide | $10 \leq 100\ \mu m$ | 321 | 46 |
| 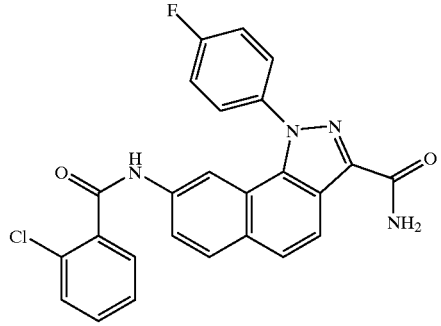 | 458.88 | 8-[(2-chlorobenzoyl)amino]-1-(4-fluorophenyl)-1H-benzo[g]indazole-3-carboxamide | $1 \leq 10\ \mu M$ | 459 | 47 |
| 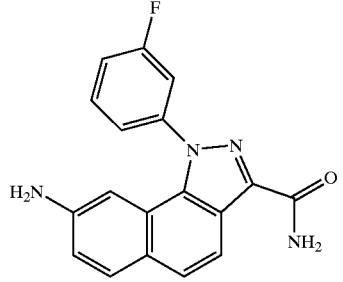 | 320.33 | 8-amino-1-(3-fluorophenyl)-1H-benzo[g]indazole-3-carboxamide | $\leq 20$ | 321 | 48 |
| 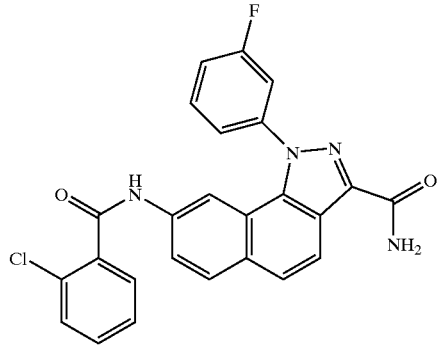 | 458.88 | 8-[(2-chlorobenzoyl)amino]-1-(3-fluorophenyl)-1H-benzo[g]indazole-3-carboxamide | $\leq 50$ | 459 | 49 |
| 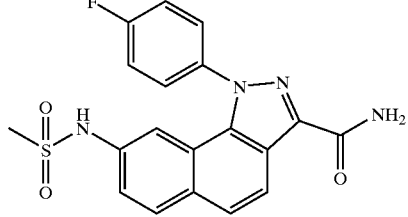 | 398.42 | 1-(4-fluorophenyl)-8-[(methylsulfonyl)amino]-1H-benzo[g]indazole-3-carboxamide | $\leq 1\ \mu M$ | 399 | 50 |

TABLE 3-continued

| Compound No., Structure | Mol. Wt. | Compound Name(s) | IKK2 Resin IC 50 | LCMS (M + H) | Example |
|---|---|---|---|---|---|
| | 459.87 | 8-{[(2-chloropyridin-3-yl)carbonyl]amino}-1-(4-fluorophenyl)-1H-benzo[g]indazole-3-carboxamide | ≦1 μM | 460 | 51 |
| | 477.86 | 8-{[(2-chloropyridin-3-yl)carbonyl]amino}-1-(2,4-difluorophenyl)-1H-benzo[g]indazole-3-carboxamide | ≦1 μM | 478 | 52 |
| | 446.49 | 1-(4-fluorophenyl)-8-{[(4-methylpiperazin-1-yl)carbonyl]amino}-1H-benzo[g]indazole-3-carboxamide | ≦20 | 447 | 53 |

Example 54

1-(1,3-benzodioxol-5-yl)-8-[(2-chlorobenzoyl)amino]-1H-benzo[g]indazole-3-carboxamide

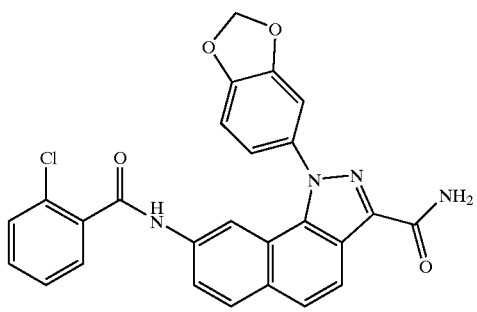

Step 1

Ethyl 1-(1,3-benzodioxol-5-yl)-8-nitro-4,5-dihydro-1H-benzo[g]indazole-3-carboxylate

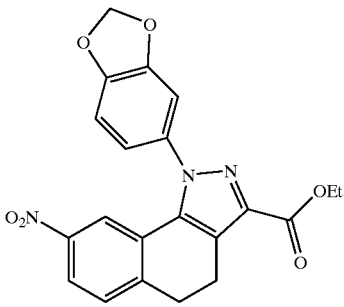

This compound was synthesized in a similar manner as described in Examples 36 step 1 using 3,4-methylenedioxyphenylhydrazine and the material of Example 1.

Step 2

Ethyl8-amino-1-(1,3-benzodioxol-5-yl)-4,5-dihydro-1H-benzo[g]indazole-3-carboxylate

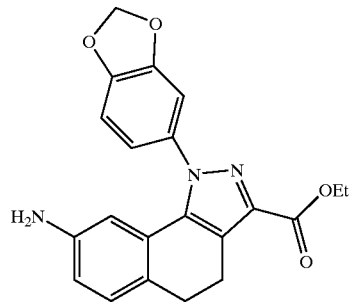

This compound was synthesized in a similar manner as described in Example 4a.

Step 3

8-amino-1-(1,3-benzodioxol-5-yl)-4,5-dihydro-1H-benzo[g]indazole-3-carboxamide

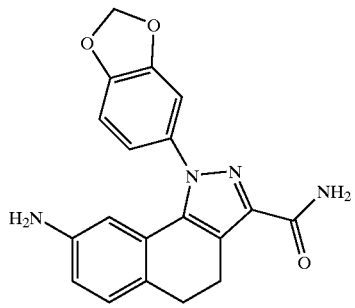

This compound was synthesized in a similar manner as described in Example 4b.

Step 4

8-amino-1-(1,3-benzodioxol-5-yl)-1H-benzo[g]indazole-3-carboxamide

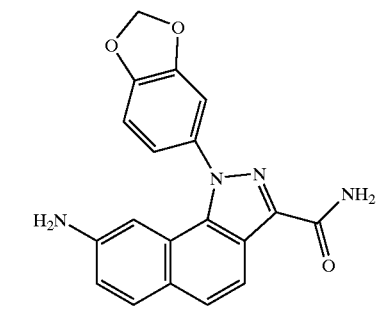

This compound was synthesized in a similar manner as described in Examples 36 step 4.

Step 5

1-(1,3-benzodioxol-5-yl)-8-[(3-chloroisonicotinoyl)amino]-1H-benzo[g]indazole-3-carboxamide

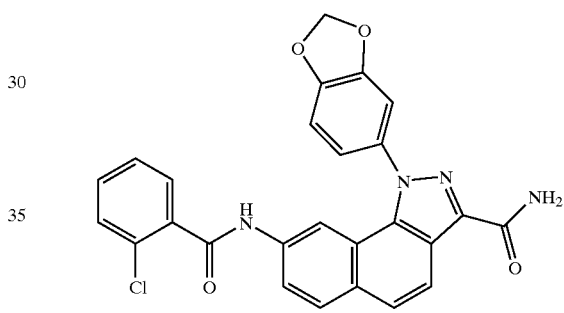

This compound was synthesized in a similar manner as described in Example 36 step 5.

The compounds of Examples 54–58 shown in Table 4 were synthesized in a similar manner as described in Examples 35, 36 and 44.

TABLE 4

| Compound No., Structure | Mol. Wt. | Compound Name(s) | IKK2 Resin IC 50 | LCMS (M + H) | Example |
|---|---|---|---|---|---|
| 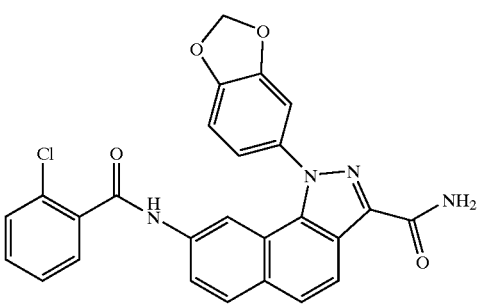 | 484.90 | 1-(1,3-benzodioxol-5-yl)-8-[(2-chlorobenzoyl)amino]-1H-benzo[g]indazole-3-carboxamide | ≦1 μM | 485 | 54 |

TABLE 4-continued

| Compound No., Structure | Mol. Wt. | Compound Name(s) | IKK2 Resin IC 50 | LCMS (M + H) | Example |
|---|---|---|---|---|---|
| | 485.89 | 1-(1,3-benzodioxol-5-yl)-8-{[(2-chloropyridin-3-yl)carbonyl]amino}-1H-benzo[g]indazole-3-carboxamide | ≦1 μM | 486 | 55 |
| | 346.35 | 8-amino-1-(1,3-benzodioxol-5-yl)-1H-benzo[g]indazole-3-carboxamide | 1 ≦ 10 μM | 347 | 56 |
| | 564.79 | 1-(1,3-benzodioxol-5-yl)-5-bromo-8-{[(2-chloropyridin-3-yl)carbonyl]amino}-1H-benzo[g]indazole-3-carboxamide | ≦1 μM | 565 | 57 |
| | 485.89 | 1-(1,3-benzodioxol-5-yl)-8-[(3-chloroisonicotinoyl)amino]-1H-benzo[g]indazole-3-carboxamide | ≦1 μM | 486 | 58 |

Biological Evaluation

Materials

SAM² ™ 96 Biotin capture plates were from Promega. Anti-FLAG affinity resin, FLAG-peptide, NP-40 (Nonidet P-40), BSA, ATP, ADP, AMP, LPS (*E. coli* serotype 0111:B4), and dithiothreitol were obtained from Sigma Chemicals. Antibodies specific for NEMO (TKKγ) (FL-419), IKK1 (H-744), IKK2 (H-470) and IκBα (C-21) were purchased from Santa Cruz Biotechnology. Ni-NTA resin was purchased from Qiagen. Peptides were purchased from American Peptide Company. Protease inhibitor cocktail tablets were from Boehringer Mannheim. Sephacryl S-300 column was from Pharmacia LKB Biotechnology. Centriprep-10 concentrators with a molecular weight cutoff of 10 kDa and membranes with molecular weight cut-off of 30 kDa were obtained from Amicon. [Y-$^{33}$P] ATP (2500 Cu/mmol) and [Y-$^{32}$P] ATP (6000 C/mmol) were purchased from Amersham. The other reagents used were of the highest grade commercially available.

Cloning and Expression cDNAs of human IKK1 and IKK2 were amplified by reverse transcriptase-polymerase chain reaction from human placental RNA (Clonetech). hIKK1 was subcloned into pFastBac HTa (Life Technologies) and expressed as N-terminal His$_6$-tagged fusion protein. The hIKK2 cDNA was amplified using a reverse oligonucleotide primer which incorporated the peptide sequence for a FLAG-epitope tag at the C-terminus of the IKK2 coding region (DYKDDDDKD). The hIKK2:FLAG cDNA was subcloned into the baculovirus vector pFastBac. The rhIKK2 (S177S, E177E) mutant was constructed in the same vector used for wild type rhIKK2 using a QuikChange™ mutagenesis kit (Stratagene). Viral stocks of each construct were used to infect insect cells grown in 40L suspension culture. The cells were lysed at a time that maximal expression and rhIKK activity were demonstrated. Cell lysates were stored at −80° C. until purification of the recombinant proteins was undertaken as described below.

Enzyme Isolation

All purification procedures were carried out at 4° C. unless otherwise noted. Buffers used are: buffer A: 20 mM Tris-HCl, pH 7.6, containing 50 mM NaCl, 20 mM NaF, 20 mM β-Glycerophosphate, 500 uM sodiumortho-vanadate, 2.5 mM metabisulfite, 5 mM benzamidine, 1 mM EDTA, 0.5 mM EGTA, 10% glycerol, 1 mM DTT, 1×Complete™ protease inhibitors; buffer B: same as buffer A, except 150 mM NaCl, and buffer C: same as buffer A, except 500 mM NaCl.

Isolation of rhIKK1 Homodimer

Cells from an 8 liter fermentation of baculovirus-expressed IKK1 tagged with His peptide were centrifuged and the cell pellet (MOI 0.1, I=72 hr) was re-suspended in 100 ml of buffer C. The cells were microfluidized and centrifuged at 100,000×g for 45 min. The supernatant was collected, imidazole added to the final concentration of 10 mM and incubated with 25 ml of Ni-NTA resin for 2 hrs. The suspension was poured into a 25 ml column and washed with 250 ml of buffer C and then with 125 ml of 50 mM imidazole in buffer C. rhIKK1 homodimer was eluted using 300 mM imidazole in buffer C. BSA and NP-40 were added to the enzyme fractions to the final concentration of 0.1%. The enzyme was dialyzed against buffer B, aliquoted and stored at −80° C.

Isolation of rhIKK2 Homodimer

A 10 liter culture of baculovirus-expressing IKK2 tagged with FLAG peptide was centrifuged and the cell pellet (MOI=0.1 and I=72 hrs) was re-suspended in buffer A. These cells were microfluidized, and centrifuged at 100,000×g for 45 min. Supernatant was passed over a G-25 column equilibrated with Buffer A. Protein peak was collected and incubated with anti-FLAG affinity resin on a rotator overnight in buffer B. The resin was washed in batch with 10–15 bed volumes of buffer C. Washed resin was poured into a column and rhIKK2 homodimer was eluted using 5 bed volumes of buffer B containing FLAG peptide. 5 mM DTT, 0.1% NP-40 and BSA (concentrated to 0.1% in final amount) was added to the eluted enzyme before concentrating in using an Amicon membrane with a molecular weight cut-off of 30 kDa. Enzyme was aliquoted and stored at −80° C.

Isolation of rhIKK1/IKK2 Heterodimer

The heterodimer enzyme was produced by coinfection in a baculovirus system (FLAG IKK2/IKK1 His; MOI=0.1 and I=72 hrs). Infected cells were centrifuged and the cell pellet (10.0 g) was suspended in 50 ml of buffer A. The protein suspension was microfluidized and centrifuged at 100,000×g for 45 min. Imidazole was added to the supernatant to a final concentration of 10 mM. The protein was allowed to bind 25 ml of Ni-NTA resin by mixing for 2 hrs. The protein-resin slurry was poured into a 25 ml column and washed with 250 ml of buffer A containing 10 mM imidazole followed by 125 ml of buffer A containing 50 mM imidazole. Buffer A, containing 300 mM imidazole, was then used to elute the protein. A 75 ml pool was collected and NP-40 was added to a final concentration of 0.1%. The protein solution was then dialyzed against buffer B. The dialyzed heterodimer enzyme was then allowed to bind to 25 ml of anti-FLAG M2 agarose affinity gel overnight with constant mixing. The protein-resin slurry was then centrifuged for 5 min at 2,000 rpm. The supernatant was collected and the resin re-suspended in 100 ml of buffer C containing 0.1% NP-40. The resin was washed with 375 ml of buffer C containing 0.1% NP-40. The protein-resin was poured into a 25 ml column and the enzyme eluted using buffer B containing FLAG peptide. Enzyme fractions (100 ml) were collected and concentrated to 20 ml using an Amicon membrane with molecular weight cut-off of 30 kDa. Bovine serum albumin was added to the concentrated enzyme to final concentration of 0.1%. The enzyme was then aliquoted and stored at −80° C.

Cell Culture

The wild type (wt) human pre-B cell line, 70Z/3, and its mutant, 1.3E2, were generously provided by Dr. Carol Sibley. Wt 70Z/3 and 1.3E2 cells were grown in RPMI 1640 (Gibco) supplemented with 7% defined bovine serum (Hyclone) and 50 μM 2-mercaptoethanol. Human monocytic leukemia THP-1 cells, obtained from ATCC, were cultured in RPMI 1640 supplemented with 10% defined bovine serum, 10 mM HEPES, 1.0 mM sodium pyruvate and 50 μM 2-mercaptoethanol. For experiments, cells were plated in 6 well plates at 1×10$^6$ cells/ml in fresh media. Pre-B cells were stimulated by the addition of 10 μg/ml LPS for varying lengths of time ranging from 0–4 hr. THP-1 cells were stimulated by the addition of 1 μg/ml LPS for 45 minutes. Cells were pelleted, washed with cold 50 mM sodium phosphate buffer, pH 7.4 containing 0.15 M NaCl and lysed at 4° C. in 20 mM Hepes buffer, pH 7.6 containing 50 mM NaCl, 1 mM EDTA, 1 mM EGTA, 1 mM sodium orthovanadate, 10 mM β-glycerophosphate, 1 mM NaF, 1 mM PMSF, 1 mM DTT and 0.5% NP40 (lysis buffer). The cytosolic fractions obtained following centrifugation at 10,000×g were stored at −80° C. until used.

Immunoprecipitation and Western Blotting

SF9 cells paste containing rhIKKs were centrifuged (100,000×g, 10 min) to remove debris. rhIKKs were immunoprecipitated (100 μg of cell paste) from the cell supernatant using 3 μg of anti-NEMO antibody (FL-419), followed by coupling to protein A sepharose beads. rhIKKs were also immunoprecipitated from affinity chromatography purified protein preparations (1 μg) using anti-FLAG, anti-His or anti-NEMO antibodies (1–4 μg) followed by protein A sepharose coupling. The native, human IKK complex was immunoprecipitated from THP-1 cell homogenates (300 μg/condition) using the anti-NEMO antibody. Immune complexes were pelleted and washed 3 times with 1 ml cold lysis buffer. Immunoprecipitated rhIKKs were chromatographed by SDS-PAGE (8% Tris-glycine) and transferred to nitrocellulose membranes (Novex) and detected by chemiluminescense (SuperSignal) using specific anti-IKK antibodies (IKK-470, IKK1H-744). Native IKK2, IκBα and NEMO proteins from cytosolic lysates (20–80 μg) were separated by SDS-PAGE and visualized by chemiluminescense using specific antibodies.

Phosphatase Treatment

Immunoprecipitated rhIKKs were washed 2 times in 50 mM Tris-HCl, pH 8.2 containing 0.1 mM EDTA, 1 mM DTT, 1 mM PMSF and 2 mM MnCl$_2$ and resuspended in 50 μl. Phosphatase (λPPase, 1000 U) was pre-diluted in the same buffer and added to the IKK samples. Following an incubation at room temperature for 30 minutes with intermittent mixing, cold lysis buffer was added to the tubes to stop the reaction. After several washes, 10% of the beads were removed for Western analysis, and the remaining material was pelleted and resuspended in 100 μl of the buffer used for the in vitro kinase assay.

IKKαSAM Enzyme Assay

IKKα kinase activity was measured using a biotinylated IκBα peptide (Gly-Leu-Lys-Lys-Glu-Arg-Leu-Leu-Asp-Asp-Arg-His-Asp-Ser$_{32}$-Gly-Leu-Asp-Ser$_{36}$-Met-Lys-Asp-Glu-Glu), a SAM$^{2\text{™}}$ 96 Biotin capture plate, and a vacuum system. The standard reaction mixture contained 5 μM biotinylated IκBα peptide, 1 μM [γ-$^{33}$P] ATP (about 1×10$^5$ cpm), 1 mM DTT, 50 mM KCl, 2 mM MgCl$_2$, 2 mM MnCl$_2$, 10 mM NaF, 25 mM Hepes buffer, pH. 7.6 and enzyme solution (1–10 μl) in a final volume of 50 μl. After incubation at 25° C. for 30 min, 25 μl of the reaction mixture was withdrawn and added to a SAM$^{2\text{™}}$ 96 Biotin capture 96-well plate. Each well was then washed successively with 800 μl 2 M NaCl, 1.2 ml of NaCl containing 1% H$_3$PO$_4$, 400 μl H$_2$O, and 200 μl 95% ethanol. The plate was allowed to dry in a hood at 25° C. for 1 hr and then 25 μl of scintillation fluid (Microscint 20) was added to each well. Incorporation of [γ-$^{33}$P] ATP was measured using a Top-Count NXT (Packard). Under each assay condition, the degree of phosphorylation of IκBα peptide substrate was linear with time and concentration for all purified enzymes. Results from the biotinylated peptide assay were confirmed by SDS-PAGE analysis of kinase reaction utilizing a GST-IκBα$_{1-54}$ and [γ-$^{32}$P] ATP. The resulting radiolabeled substrate was quantitated by Phosphoimager (Molecular Dynamics). An ion exchange resin assay was also employed using [γ-$^{33}$P] ATP and GST-IκBα$_{1-54}$ fusion protein as the substrates. Each assay system yielded consistent results in regard to K$_m$ and specific activities for each of the purified kinase isoforms. One unit of enzyme activity was defined as the amount required to catalyze the transfer of 1 nmole of phosphate from ATP to IκBα peptide per min. Specific activity was expressed as units per mg of protein. For experiments related to K$_m$ determination of purified enzymes, various concentrations of ATP or IκBα peptide were used in the assay at either a fixed IκBα or ATP concentration. For IκBα peptide K$_m$, assays were carried out with 0.1 μg of enzyme, 5 μM ATP and IκBα peptide from 0.5 to 20 μM. For ATP K$_m$, assays were carried out with 0.1 μg of enzyme, 10 μM IκBα peptide and ATP from 0.1 to 10 μM. For K$_m$ determination of rhIKK1 homodimer, due to its low activity and higher K$_m$ for IκBα peptide, rIKK1 homodimer (0.3 μg) was assayed with 125 μM IκBα peptide and a 5-fold higher specific activity of ATP (from 0.1 to 10 μM) for ATP K$_m$ experiments and a 5-fold higher specific activity of 5 μM ATP and IκBα peptide (from 5 to 200 μM) for IκBα peptide K$_m$ experiments.

IKKβ Resin Enzyme Assay

IKKβ kinase activity was measured using a biotinylated IκBα peptide (Gly-Leu-Lys-Lys-Glu-Arg-Leu-Leu-Asp-Asp-Arg-His-Asp-Ser$_{32}$-Gly-Leu-Asp-Ser$_{36}$-Met-Lys-Asp-Glu-Glu) (American Peptide Co.). 20 ul of the standard reaction mixture contained 5 μM biotinylated IκBα peptide, 0.1 μCi/reaction [γ-$^{33}$P] ATP (Amersham) (about 1×10$^5$ cpm), 1 μM ATP (Sigma), 1 mM DTT (Sigma), 2 mM MgCl$_2$ (Sigma), 2 mM MnCl$_2$ (Sigma), 10 mM NaF (Sigma), 25 mM Hepes (Sigma) buffer, pH 7.6 and 20 μl enzyme solution and 10 ul inhibitor in a final volume of 50 μl. After incubation at 25° C. for 30 min, 150 μl resin (Dowex anion-exchange resin AG1X8 200–400 mesh) in 900 mM formate, pH 3.0 was added to each well to stop the reaction. Resin was allowed to settle for one hour and 50 ul of supernatant was removed to a Micolite-2 flat bottom plate (Dynex). 150 μl of scintillation fluid (Microscint 40) (Packard) was added to each well. Incorporation of [γ-$^{33}$P] ATP was measured using a Top-Count NXT (Packard).

IKK Heterodimer Resin Enzyme Assay

IKK heterodimer kinase activity was measured using a biotinylated IκBα (peptide (Gly-Leu-Lys-Lys-Glu-Arg-Leu-Leu-Asp-Asp-Arg-His-Asp-Ser$_{32}$-Gly-Leu-Asp-Ser$_{36}$-Met-Lys-Asp-Glu-Glu) (American Peptide Co.). 20 ul of the standard reaction mixture contained 5 μM biotinylated IκBα peptide, 0.1 μCi/reaction [γ-$^{33}$P] ATP (Amersham) (about 1×10$^5$ cpm), 1 μM ATP (Sigma), 1 mM DTT (Sigma), 2 mM MgCl$_2$ (Sigma), 2 mM MnCl$_2$ (Sigma), 10 mM NaF (Sigma), 25 mM Hepes (Sigma) buffer, pH 7.6 and 20 μl enzyme solution and 10 μl inhibitor in a final volume of 50 μl. After incubation at 25° C. for 30 min, 150 μl resin (Dowex anion-exchange resin AG1X8 200–400 mesh) in 900 mM formate, pH 3.0 was added to each well to stop the reaction. Resin was allowed to settle for one hour and 50 ul of supernatant was removed to a Micolite-2 flat bottom plate (Dynex). 150 μl of scintillation fluid (Microscint 40) (Packard) was added to each well. Incorporation of [γ-$^{33}$P] ATP was measured using a Top-Count NXT (Packard).

What is claimed is:

1. A compound of Formula II:

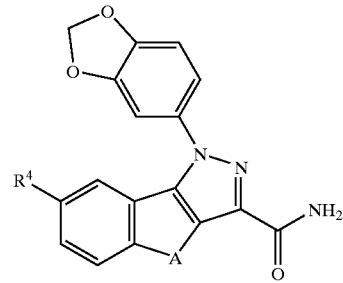

II wherein

A is $(CH_2)_m$—$CR^{15}$=$CR^{16}$—$(CH_2)_m$;

m is independently selected from 0, 1, or 2;

$R^4$ is selected from the group consisting of: halogen, alkylsulfinyl, alkylsulfonyl, cyano, alkoxycarbonyl, alkyl, haloalkyl, hydrido, hydroxyalkyl, haloalkoxy, heterocyclic, nitro, acylamino, aryl, heteroaryl, and alkenyl, $OR^{13}$, $SR^8$, $SO_2N(R^8)R^{8'}$, $NHR^9$, $NHCOR^9$, $NR^9COR^9$, $NHCO(OR^9)$, $NR^9CO(OR^9)$, $NR^8SO_2R^{10}$, $NHSO_2N(R^{10})R^{10'}$, $NR^6CON(R^{10})R^{10'}$, $COR^9$, $CO_2R^8$, $CON(R^8)R^{8'}$, wherein $R^8$ and $R^{8'}$ may be taken together to form a 3–7 membered carbocyclic ring having 1 to 3 substituted or unsubstituted heteroatoms selected from S, SO, SO$_2$, O, N, and $NR^6$, and wherein $R^{10}$ and $R^{10'}$ may be taken together to form a 3–7 membered carbocyclic ring having 1 to 3 substituted or unsubstituted heteroatoms selected from S, SO, SO$_2$, O, N, and $NR^6$ wherein said aryl, heterocyclic, heteroaryl, or alkenyl are optionally substituted with $R^9$;

$R^6$ is independently selected from the group consisting of: hydrido, aryl, heteroaryl, lower alkyl, haloalkyl, alkenyl, alkynyl, hydroxyalkyl, aminoalkyl, alkylaminoalkyl, alkoxy, alkoxyalkyl, heterocyclicalkyl, and heterocyclic;

$R^8$ is independently selected from the group consisting of: hydrido, aryl, heteroaryl, arylalkyl, heterocyclic, haloalkyl, arylalkylamino, alkylaminoalkyl, dialkylaminoalkyl, alkyl, alkenyl, alkynyl, heteroarylalkyl, and heterocyclicalkyl;

$R^{8'}$ is independently selected from the group consisting of: hydrido, aryl, heteroaryl, arylalkyl, heterocyclic, haloalkyl, arylalkylamino, alkylaminoalkyl, dialkylaminoalkyl, alkyl, alkenyl, alkynyl, heteroarylalkyl, and heterocyclicalkyl;

$R^9$ is independently selected from the group consisting of: hydrido, lower alkyl, aryl, heteroaryl, arylalkyl, heterocyclic, cycloalkyl, heterocyclicalkyl, haloalkyl, arylalkylamino, amino, aminoalkyl, aminoacyl, nitro, azido, and heteroarylalkyl, wherein alkyl, aryl, heteroaryl, aminoalkyl, or arylalkyl are optionally substituted with one or more radical selected from the group consisting of: alkylsulfonamide, sulfamyl, alkyl, alkylthio, alkylsulfinyl, alkylsulfonyl, alkylamino, aminoalkyl, alkylaminoalkyl, alkoxy, halogen, acyloxy, oxy, formyl, haloalkyl, cyano, haloalkoxy, acyl, carboxyl, hydroxy, hydroxyalkyloxy, phenoxy, nitro, azido, benzyloxy, dialkylaminoacyl, thioalkyl, aminoacyloxy, thiocyanate, isothiocyanate, alkyldioxy, hydroxyalkyl, alkylamino, alkyloxycarbonyl, alkoxyalkyl, alkenylamino, alkynylamino, alkenyl, alkynyl, dialkylaminoalkyloxy, and heterocyclic optionally substituted with alkyl, alkylamino, aminoalkyl, hydroxyalkyl, and alkylaminoalkyl;

$R^{10}$ is independently selected from the group consisting of: hydrido, lower alkyl, heteroaryl, heterocyclic, haloalkyl, arylalkylamino, heteroarylalkyl, aryl, and arylalkyl, wherein aryl, heteroaryl, heterocyclic, or arylalkyl are optionally substituted with one or more radical selected from alkyl, alkoxy, halogen, haloalkyl, cyano, haloalkoxy, acyl, carboxyl, hydroxy, hydroxyalkyloxy, phenoxy, benzyloxy, dialkylaminoalkyloxy, and heterocyclic;

$R^{10'}$ is independently selected from the group consisting of: hydrido, lower alkyl, heteroaryl, heterocyclic, haloalkyl, arylalkylamino, heteroarylalkyl, aryl, and arylalkyl, wherein aryl, heteroaryl, heterocyclic, or arylalkyl are optionally substituted with one or more radical selected from alkyl, alkoxy, halogen, haloalkyl, cyano, haloalkoxy, acyl, carboxyl, hydroxy, hydroxyalkyloxy, phenoxy, benzyloxy, dialkylaminoalkyloxy, and heterocyclic;

$R^{13}$ is selected from the group consisting of: hydrido, alkyl, aryl, arylalkyl, heteroaryl, heterocyclicalkyl, and heteroarylalkyl, wherein aryl, alkyl, arylalkyl, heteroaryl, heterocyclicalkyl, or heteroarylalkyl are optionally substituted with one or more radicals selected from the group consisting of $OR^{14}$, $N(R^{14})R^{14'}$, and glycols;

$R^{14}$ is independently selected from the group consisting of hydrido, and lower alkyl;

$R^{14'}$ is independently selected from the group consisting of hydrido, and lower alkyl;

$R^{15}$ is selected from the group consisting of: hydrido, halogen, alkyl, cycloalkyl, aryl, haloalkyl, heteroaryl, heterocyclic, alkylalkene, alkylalkyne, hydroxy, hydroxyalkyl, alkylhydroxy, amino, aminoalkyl, alkylamino, alkylaminoalkyl, alkylhydroxyalkyl, nitro, cyano, alkylthio, alkylsulfinyl, alkylsulfonyl; wherein aryl or arylalkyl are optionally substituted with one or more radical selected from alkyl, alkoxy, halo, haloalkyl, cyano, haloalkoxy, acyl, carboxyl, hydroxy, hydroxyalkyloxy, phenoxy, benzyloxy, dialkylaminoalkyloxy, heterocyclic; and $R^{16}$ is selected from the group consisting of: hydrido, halogen, alkyl, cycloalkyl, aryl, haloalkyl, heteroaryl, heterocyclic, alkylalkene, alkylalkyne, hydroxy, hydroxyalkyl, alkylhydroxy, amino, aminoalkyl, alkylamino, alkylaminoalkyl, alkylhydroxyalkyl, nitro, cyano, alkylthio, alkylsulfinyl, alkylsulfonyl; wherein aryl or arylalkyl are optionally substituted with one or more radical selected from alkyl, alkoxy, halo, haloalkyl, cyano, haloalkoxy, acyl, carboxyl, hydroxy, hydroxyalkyloxy, phenoxy, benzyloxy, dialkylaminoalkyloxy, heterocyclic; wherein $R^{15}$ and $R^{16}$ may be taken together to form a 5 to 7 membered saturated or unsaturated carbocyclic ring optionally containing 0 to 3 heteroatoms selected from the group consisting of N, O, or S, and wherein said ring is optionally substituted with $R^1$;

or tautomers or pharmaceutically acceptable salts thereof.

2. The compound of claim 1 of the Formula:

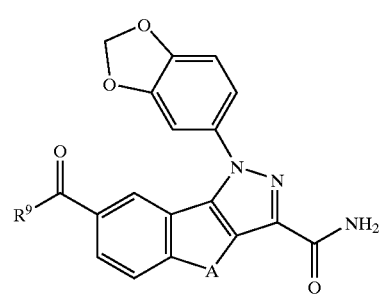

II wherein

A is $(CH_2)_m$—$CR^{15}$=$CR^{16}$—$(CH_2)_m$;

m is independently selected from 0, 1, or 2;

$R^9$ is independently selected from the group consisting of: hydrido, lower alkyl, aryl, heteroaryl, arylalkyl, heterocyclic, cycloalkyl, heterocyclicalkyl, haloalkyl, arylalkylamino, amino, aminoalkyl, aminoacyl, nitro, azido, and heteroarylalkyl, wherein alkyl, aryl, heteroaryl, aminoalkyl, or arylalkyl are optionally substituted with one or more radical selected from the group consisting of: alkylsulfonamide, sulfamyl, alkyl, alkylthio, alkylsulfinyl, alkylsulfonyl, alkylamino, aminoalkyl, alkylaminoalkyl, alkoxy, halogen, acyloxy, oxy, formyl, haloalkyl, cyano, haloalkoxy, acyl, carboxyl, hydroxy, hydroxyalkyloxy, phenoxy, nitro, azido, benzyloxy, dialkylaminoacyl, thioalkyl, aminoacyloxy, thiocyanate, isothiocyanate, alkyldioxy, hydroxyalkyl, alkylamino, alkyloxycarbonyl, alkoxyalkyl, alkenylamino, alkynylamino, alkenyl, alkynyl, dialkylaminoalkyloxy, and heterocyclic optionally substituted with alkyl, alkylamino, aminoalkyl, hydroxyalkyl, and alkylaminoalkyl;

$R^{15}$ is selected from the group consisting of: hydrido, halogen, alkyl, cycloalkyl, aryl, haloalkyl, heteroaryl, heterocyclic, alkylalkene, alkylalkyne, hydroxy, hydroxyalkyl, alkylhydroxy, amino, aminoalkyl, alkylamino, alkylaminoalkyl, alkylhydroxyalkyl, nitro, cyano, alkylthio, alkylsulfinyl, alkylsulfonyl; wherein aryl or arylalkyl are optionally substituted with one or more radical selected from alkyl, alkoxy, halo, haloalkyl, cyano, haloalkoxy, acyl, carboxyl, hydroxy, hydroxyalkyloxy, phenoxy, benzyloxy, dialkylaminoalkyloxy, heterocyclic; and $R^{16}$ is selected from the group consisting of: hydrido, halogen, alkyl, cycloalkyl, aryl, haloalkyl, heteroaryl, heterocyclic, alkylalkene, alkylalkyne, hydroxy, hydroxyalkyl, alkylhydroxy, amino, aminoalkyl, alkylamino, alkylaminoalkyl, alkylhydroxyalkyl, nitro, cyano, alkylthio, alkylsulfinyl, alkylsulfonyl; wherein aryl or arylalkyl are optionally substituted with one or more radical selected from alkyl, alkoxy, halo, haloalkyl, cyano, haloalkoxy, acyl, carboxyl, hydroxy, hydroxyalkyloxy, phenoxy, benzyloxy, dialkylaminoalkyloxy, heterocyclic; wherein $R^{15}$ and $R^{16}$ may be taken together to form a 5 to 7 membered saturated or unsaturated carbocyclic ring optionally containing 0 to 3 heteroatoms selected from the group consisting of N, O, or S, and wherein said ring is optionally substituted with $R^1$;

or tautomers or pharmaceutically acceptable salts thereof.

3. The compound of claim 2 selected from the group selected from the group consisting of:

1-(1,3-benzodioxol-5-yl)-8-[(2-chlorobenzoyl)amino]-1H-benzo[g]indazole-3-carboxamide, 1-(1,3-benzodioxol-5-yl)-8-{[(2-chloropyridin-3-yl)carbonyl]amino}-1H-benzo[g]indazole-3-carboxamide, 8-amino-1-(1,3-benzodioxol-5-yl)-1H-benzo[g]indazole-3-carboxamide, 1-(1,3-benzodioxol-5-yl)-5-bromo-8-{[(2-chloropyridin-3-yl)carbonyl]amino}-1H-benzo[g]indazole-3-carboxamide, and 1-(1,3-benzodioxol-5-yl)-8-[(3-chloroisonicotinoyl)amino]-1H-benzo[g]indazole-3-carboxamide.

* * * * *